(12) United States Patent
Bowman et al.

(10) Patent No.: US 11,950,878 B2
(45) Date of Patent: Apr. 9, 2024

(54) METHODS FOR ESTABLISHING THE STIFFNESS OF A BONE USING MECHANICAL RESPONSE TISSUE ANALYSIS

(71) Applicant: Ohio University, Athens, OH (US)

(72) Inventors: Lyn Bowman, Athens, OH (US); Anne B. Loucks, Athens, OH (US)

(73) Assignee: Ohio University, Athens, OH (US)

( * ) Notice: Subject to any disclaimer, the term of this patent is extended or adjusted under 35 U.S.C. 154(b) by 844 days.

(21) Appl. No.: 16/964,464

(22) PCT Filed: Jan. 23, 2019

(86) PCT No.: PCT/US2019/014662
§ 371 (c)(1),
(2) Date: Jul. 23, 2020

(87) PCT Pub. No.: WO2019/147608
PCT Pub. Date: Aug. 1, 2019

(65) Prior Publication Data
US 2021/0045636 A1 Feb. 18, 2021

Related U.S. Application Data

(60) Provisional application No. 62/621,204, filed on Jan. 24, 2018.

(51) Int. Cl.
*A61B 5/00* (2006.01)
*G16H 40/67* (2018.01)
(Continued)

(52) U.S. Cl.
CPC .......... *A61B 5/0051* (2013.01); *A61B 5/4509* (2013.01); *A61B 5/7282* (2013.01);
(Continued)

(58) Field of Classification Search
CPC ..... A61B 5/0051; A61B 5/4509; G16H 50/30
See application file for complete search history.

(56) References Cited

U.S. PATENT DOCUMENTS

| 5,006,984 A | 4/1991 | Steele |
| 5,487,395 A | 1/1996 | Strowe |

(Continued)

FOREIGN PATENT DOCUMENTS

| WO | 2012089221 A1 | 7/2012 |
| WO | 2014169217 A3 | 11/2015 |
| WO | 2019147608 A1 | 8/2019 |

OTHER PUBLICATIONS

Communication pursuant to Article 94(3) EPC dated Dec. 21, 2022, pertaining to EP Patent Application No. 19743699.1, 5 pgs.
(Continued)

*Primary Examiner* — Alex M Valvis
*Assistant Examiner* — Jonathan M Haney
(74) *Attorney, Agent, or Firm* — Dinsmore & Shohl LLP

(57) ABSTRACT

Parametric model based computer implemented methods for determining the stiffness of a bone, systems for estimating h the stiffness of a bone in vivo, and methods for determining the stiffness of a bone. The computer implemented methods include determining a complex compliance frequency response function Y(f) and an associated complex stiffness frequency response function H(f) and independently fitting a parametric mathematical model to Y(f) and to H(f), and using a first measure of conformity and a second measure of conformity of the collected data to determine accuracy and repeatability of measurements. The systems include a device for measuring the stiffness of the bone in vivo and a data analyzer to determine a complex compliance frequency response function Y(f) and an associated complex stiffness frequency response function H(f).

9 Claims, 11 Drawing Sheets

(51) Int. Cl.
G16H 50/20 (2018.01)
G16H 50/30 (2018.01)
G16H 50/70 (2018.01)

(52) U.S. Cl.
CPC ............. *G16H 40/67* (2018.01); *G16H 50/20* (2018.01); *G16H 50/30* (2018.01); *G16H 50/70* (2018.01)

(56) References Cited

U.S. PATENT DOCUMENTS

| | | | |
|---|---|---|---|
| 5,836,876 | A | 11/1998 | Dimarogonas |
| 6,183,425 | B1* | 2/2001 | Whalen ................ A61B 5/1038 600/595 |
| 7,485,100 | B2 | 2/2009 | Garcia-Webb et al. |
| 9,245,069 | B2 | 1/2016 | Keyak |
| 10,299,719 | B2* | 5/2019 | Bowman .............. A61B 5/0051 |
| 11,324,440 | B2* | 5/2022 | Bowman .............. A61B 5/7253 |
| 2002/0082779 | A1 | 6/2002 | Ascenzi |
| 2006/0069318 | A1* | 3/2006 | Keaveny ................. G06T 7/97 703/11 |
| 2006/0224088 | A1 | 10/2006 | Roche |
| 2008/0208550 | A1 | 8/2008 | Ascenzi |
| 2010/0069455 | A1 | 3/2010 | Takato et al. |
| 2011/0270313 | A1 | 11/2011 | Justis et al. |
| 2013/0204164 | A1 | 8/2013 | Hansma et al. |
| 2016/0058365 | A1 | 3/2016 | Bowman et al. |
| 2017/0095195 | A1 | 4/2017 | Hunter et al. |

OTHER PUBLICATIONS

International Search Report and Written Opinion dated Apr. 11, 2019, pertaining to Application No. PCT/US19/14662 filed Jan. 23, 2019, 15 pgs.

International Search Report and Written Opinion pertaining to International Application No. PCT/US2018/056479 dated Dec. 21, 2018, 11 pgs.

Altenburger et al., "Mathematical Modeling of Skin-Bone Systems in Mechanical Response Tissue Analysis", Ohio University Student Expo 2011, May 13, 2011.

Charlton et al., "Accuracy of Mechanical Response Tissue Analysis (MRTA) Measurements on an Artificial Human Ulna", Ohio University Student Expo 2011, May 13, 2011.

Cotton, Jr. et al., "Ulna Simulation Assesses sensitivity to bone elastic modulus variations in a MRTA test", Abstract presented at 2012 American Society of Biomechanics 36 Annual Meeting from Aug. 15, 2012-Aug. 18, 2012, Abstract saved online at http://www.asbweb.org/conferences/2012/topics/index.html between May 10, 2012-May 11, 2012; pp. 231-232.

Kontulainen et al., "Strength indices from pQCT imaging predict up to 85% of variance in bone failure properties at tibial epiphysis and diaphysis", J. Musculoskelet Neuronal Interact, vol. 8, No. 4, pp. 401-409, Oct. 2008.

Magland et al., "Computationally-Optimized Bone Mechanical Modeling from High-Resolution Structural Images", PLoS One, vol. 7, Issue 4, Apr. 25, 2012.

"MIT and Ohio University Use Vibration in Research", The Modal Shop, Inc. News and Events, Jan. 9, 2013, www.modalshop.com/news.asp?P=MIT_And_Ohio_University_Uswe_Vibration_in_Research&NID=137.

Van Horne et al., "Precision of Mechanical Response Tissue Analysis (MRTA) Measurements", Ohio University Student Expo 2011, May 13, 2011.

Xu et al., "Flexural Rigidity and Shear Stiffness of Flagella Estimated from Induced Bends and Counterbends", Biophysical Journal 111, pp. 2759-2768, Jun. 22, 2016.

Search and Written Opinion pertaining to Application No. PCT/US2014/033816 dated Nov. 13, 2014.

International Preliminary Report on Patentability pertaining to Application No. PCT/US2014/033816 dated Oct. 13, 2015.

Search and Written Opinion pertaining to Application No. PCT/US2018/031981 dated Aug. 8, 2018.

Search and Written Opinion pertaining to Application No. PCT/US2019/014662 dated Apr. 11, 2019.

Office Action pertaining to Application No. EP14783154.9 dated Nov. 27, 2015.

* cited by examiner

METHODS FOR ESTABLISHING THE STIFFNESS OF A BONE USING MECHANICAL RESPONSE TISSUE ANALYSIS

CROSS REFERENCE TO RELATED APPLICATION

This application claims priority to U.S. Provisional Ser. No. 62/621,204 filed on Jan. 24, 2018, the entire disclosure of which is hereby incorporated by reference.

FIELD

This application generally relates to in-vivo determination of bone stiffness. Specifically, this application relates to systems and methods for establishing the stiffness of an ulna using improvements to mechanical response tissue analysis (MRTA) known as cortical bone mechanics technology (CBMT) including a two factor measure of conformity between a mathematical model and patient specific in-vivo collected data.

BACKGROUND

Bone health affects the overall health and quality of life of people around the world; for example, over 1.5 million older Americans suffer fractures due to weak bones each year. The bony skeleton provides support, mobility, and protection to the body, and serves as a storage area for essential minerals such as calcium, phosphorus and magnesium. Bone is a composite material made up of protein, minerals, and living bone cells. Collagen protein serves as the framework of the bone and provides resilience and ductility. The minerals, in the form of crystals dispersed around and between collagen fibers, stiffen the bone's protein structure.

There are two types of bone: cortical (compact) and cancellous (trabecular). Cortical bone is configured for support and protection and is arranged as densely packed parallel collagen fibrils organized in layers. This dense cortical bone is located, for example, on the surfaces of all bones and in the shafts (diaphyses) of the long and short bones of the extremities. Cancellous (trabecular) bone is comprised of an intercalated network of thin bone plates similar to a honeycomb located, for example, within the ends (epiphyses) of long bones and within the vertebrae. Cancellous bone provides strength without adding much weight, as it is configured to transfer stresses to the stronger, more massive cortical bone. In the skeleton of a young, healthy adult, cancellous bone has 80% of bone surface area, whereas cortical bone has 80% of bone mass.

Bone is a living tissue that is constantly turning over and regenerating throughout the lifespan. Old bone is broken down (resorbed), creating a void, and new bone is formed in the void. Under normal conditions there is a continuous cyclic remodeling of bone, where specialized cells called osteoclasts remove old and micro damaged bone by acidification and proteolytic digestion, and other specialized cells called osteoblasts secrete collagen and other specialized matrix proteins to synthesize new bone. Many hormones, including vitamin D, parathyroid hormone, calcitonin, estrogen, and testosterone, are involved in the regulation and complex interaction between the skeleton, intestine, and kidneys to maintain protein and mineral for homeostasis in the body (bones). Overall bone health largely relies on the proper balance of such hormones. Additionally, adequate nutrition and high impact physical activity are contributors to adequate bone health. During childhood and through the teenage years, normal healthy bones experience more bone formation than resorption. However, as humans age, increased bone resorption, decreased bone formation, or a combination of both, lead to a weakening of bones as the net result is less bone formation than resorption.

Further, bone diseases may disrupt normal bone functioning and can make bones weak. One common bone disease is osteoporosis. Osteoporosis is a skeletal disorder characterized by decreased bone strength predisposing to an increased risk of fracture. The mechanisms of osteoporosis are mediated by a disorder in the routine turnover of bone tissue on internal and external bone surfaces such that the rate at which old bone is resorbed by osteoclasts exceeds the rate at which new bone is formed by osteoblasts. These same types of cells also resorb old bone and form new bone as they repair millions of micro-cracks caused by the routine mechanical loading of the skeleton. In cortical bone, these repairs end with the creation of new intra-cortical surface area in the form of canals carrying blood vessels. Because most bone surface area in young adults is in cancellous bone, osteoporosis begins with the loss of primarily cancellous bone in sites such as the hips, spine, and wrists and only a small loss of cortical bone. Later in life, after much of the surface area in cancellous bone has been lost by the entire resorption of its thin plates, and after bone repair has created much new surface area inside millions of intra-cortical canals, most bone surface area is in cortical bone and osteoporosis becomes characterized by the loss of primarily cortical bone. As a result, after age 60, a majority of fractures occur at non-vertebral sites of primarily cortical bone.

The strength of bone depends on the quality of the bone including the architecture, turnover, damage accumulation, and mineralization of the bone. Areal bone mineral density (aBMD) describes the amount of mineral per area measured and is believed to account for only approximately 70% of bone strength. Current techniques used for clinical purposes to diagnose osteoporosis and identify fracture risk focus primarily on measuring aBMD. One such technique of measuring aBMD is Dual-energy X-ray absorptiometry (DXA). DXA noninvasively measures the transmission of x-rays with high and low energy photons through the body. A DXA measurement represents the sum of cortical and trabecular bone within the bone area scanned as part of the procedure. The results of a DXA scan are presented as a Z score and a T score, where the Z score is the number of standard deviations the measured aBMD result is from the mean for age and sex and the T score compares the measured aBMD result with the average aBMD of healthy young women.

Other radiation absorption techniques are used for research purposes only to measure volumetric bone mineral density (vBMD). These include peripheral quantitative computed tomography (pQCT) and high resolution peripheral quantitative computed tomography (HRpQCT), in which 2-dimensional DXA images are made from many different angles around the body or limb and processed by a computer to create a 3-dimensional representation of a body part. These 3-dimensional measurements of vBMD and structure can be used as inputs for estimating bone stiffness and strength by finite element analysis.

However, such techniques of measuring aBMD and vBMD are limited in that they are not capable of providing direct measures of the mechanical properties of the bone. Moreover, the mechanical properties of the bone can change while bone mineral density is unaffected, and bone mineral density can change while the mechanical properties of the bone are unaffected. Thus, changes in fracture risk may go undetected or be exaggerated by such conventional screening methods.

Techniques for direct biomechanical testing of bone have also been developed. Direct biomechanical testing of bone is desired in that it provides information about mechanical integrity of bone. Currently, quasistatic mechanical testing (QMT) is the gold standard for directly measuring the stiffness and strength of materials, including bone. QMT measures the force required to deform a bone at a very slow speed, that is, at a very low strain rate, versus the associated displacement. QMT can be utilized in the performance of many differing types of mechanical tests such as, e.g., 3-point bending. To perform 3-point bending, or flexure tests, the specimen (bone) is supported at each end, and a force is applied at the midspan, where the sensitivity is greatest to the elastic modulus and other mechanical properties at that site. As the bone bends, fibers near the top surface undergo compressive forces and the fibers near the lower surface experience tensile forces.

Bone bending strength represents the maximum bending force a bone can bear before it breaks. Bone bending strength is measured with QMT as the peak force prior to fracture in a bending test, which occurs in the plastic region of the bone. The plastic region is the area under a force-displacement curve where permanent damage is accumulating within the bone, whereas the elastic region represents the area under a force-displacement curve where no permanent damage is being done and the bone will return to its original shape when the force is released. Bone bending stiffness ($K_B$) is the resistance of a bone to bending and can be measured, for example, by QMT by applying increasing forces to the bone and measuring the slope of the force displacement curve in the elastic region of the bone. By increasing forces at a very slow speed, QMT prevents measurements of stiffness from being confounded by viscous and inertial effects.

QMT is limited in that it can only be used on excised bones and bone samples. More particularly, although QMT can make direct measurements of bone bending strength and stiffness, its use in vivo is limited in that: (1) QMT is not able to differentiate between skin compression and bone bending, which may result in an inaccurate estimation of bone displacement; and (2) measurement of bone strength by QMT requires fracturing of the bone. However, it is well known that measurements of bone bending stiffness accurately predict measurements of bone bending strength.

A technique for direct mechanical testing of bone in vivo is known as microindentation or reference point indentation (RPI). RPI measures the distance a small stylus is forcibly driven into cortical bone tissue on the surface of a bone, commonly near the mid-span of a long bone. To enable this test to be made, a local anesthetic is administered to the skin over the bone, an incision through the skin is made down to the bone, the local surface of the bone is exposed, and the outer membrane (periosteum) of the bone is removed. After the test, this incision is closed. Research has found little correlation ($R^2 \leq 0.33$) between such local RPI measurements of indentation distance and any mechanical property of whole bone measured by QMT. Thus, the inventors recognize a need for improved methods and systems for assessing the stiffness of whole bone in vivo.

SUMMARY

It is against this background that the present disclosure provides methods for determining the stiffness of a bone in vivo.

In various embodiments, a parametric model based computer implemented method for determining the stiffness of a bone is disclosed. The computer implemented method includes (1) applying a superposition of static and oscillatory forces (F) over a range of frequencies (f) to a region of a skin-bone complex thereby exciting oscillatory accelerations (a) over the range of frequencies (f) of the skin-bone complex; (2) receiving measurement data of the oscillatory forces (F) as obtaining functions of time F(t) and the resulting oscillatory acceleration data (a) as functions of time a(t) with a data receiver communicatively coupled to a controller including a processor and a storage medium containing computer readable and executable instructions; (3) repeating step (1)-(2), such that the static and oscillatory forces (F) in step (1) are applied to a shifted region of the skin-bone complex, thereby obtaining a parameter set for the shifted region of the skin-bone complex; (4) repeating step (3) until an optimized parameter set is determined based on a first measure of conformity below a predetermined first threshold value and a second measure of conformity below a predetermined second threshold value; and (5) determining the stiffness of the bone from ($K_B$) values of the optimized parameter set. When executed by the processor, the computer readable and executable instructions cause the controller to automatically: (i) transform a(t) and F(t) to functions of frequency, a(f) and F(f), (ii) reduce a(f) and F(f) to accelerance frequency response function data A(f), (iii) determine, a complex compliance frequency response function, Y(f) and associated complex stiffness frequency response function H(f), (iv) fit a parametric mathematical model to Y(f), by iteratively convergent operations, to obtain a first complete and fully converged set of parameters of the parametric mathematical model, including the stiffness of the bone ($K_B$), (v) independently fit the parametric mathematical model to H(f), by iteratively convergent operations, to obtain a second complete and fully converged set of parameters of the parametric mathematical model, including the stiffness of the bone ($K_B$), (vi) after fitting, determine discrepancies between each parameter of the first complete and fully converged set of parameters and the second complete and fully converged set of parameters as the first measure of conformity thereof to the parametric mathematical model, (vii) determine the second measure of conformity between the skewness and kurtosis of the bone peak in the complex compliance frequency response function and the parametric mathematical model, and (viii) save the first measure of conformity, the first complete and fully converged set of parameters, the second complete and fully converged set of parameters, and the second measure of conformity as a parameter set for the measured region of the skin-bone complex.

In other embodiments, a system for estimating the stiffness of a bone in vivo is disclosed. The system includes a device for measuring the stiffness of the bone in vivo and a data analyzer. The device for measuring the stiffness of the bone in vivo includes a bone positioning support, a mechanical force applicator, and a frequency response recorder, in which the bone positioning support is configured to position and support a skin-bone complex in an orientation and position for measurement. The mechanical force applicator includes a static and oscillatory force generator, static and oscillatory force sensors, an acceleration sensor and a force probe and is configured to apply a superposition of controlled static and oscillatory forced (F) over a range of frequencies (f) to a region of the skin-bone complex, wherein the oscillatory forces (F) excite oscillatory accelerations (a) of the skin-bone complex. The frequency response recorder is configured to measure and transmit to the data analyzer the oscillatory forces as functions of time F(t) and the oscillatory accelerations as functions of time a(t). The data analyzer is communicatively coupled to the static and oscillatory force generator, the static and oscillatory force sensors, the acceleration sensor, and frequency response recorder. The data analyzer includes a storage medium containing computer readable and executable instructions for collecting the transmitted oscillatory forces as functions of time F(t) and oscillatory accelerations as functions of time a(t) of the skin-bone complex, the storage medium storing a parametric mathematical model of the skin-bone complex. The data analyzer also includes a processor for executing the instructions to transform a(t) and F(t) to functions of frequency, a(f) and F(f), to reduce a(f) and F(f) to acceleration frequency response data A(f), to determine a complex compliance frequency response function Y(f) and associated complex stiffness frequency response function H(f), to fit the parametric mathematical model to Y(f) to obtain a first complete and fully converged set of parameters of the parametric mathematical model, including the stiffness of the bone ($K_B$), to independently fit the parametric mathematical model to H(f) to obtain a second complete and fully converged set of parameters of the parametric mathematical model, including the stiffness of the bone ($K_B$), and to determine the discrepancies between the first set of parameters and the second complete and fully converged set of parameters as a first measure of conformity thereof to the parametric mathematical model. The processor also determines a second measure of conformity between the skewness and kurtosis of the bone peak in the complex compliance frequency response function and the parametric mathematical model.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein.

Figure 1:
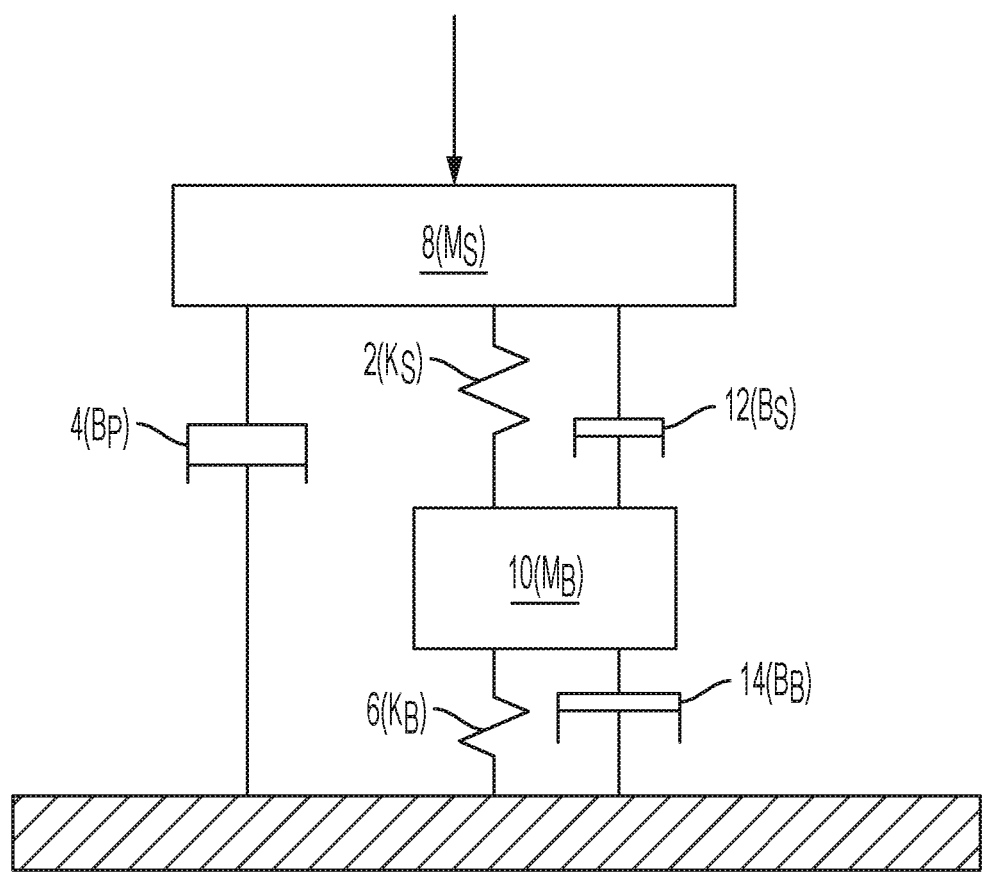
FIG. 1 depicts a schematic of a model of a skin-bone complex.

The provided drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several embodiments of the invention, and together with the description serve to explain the principles of the invention; it being understood, however, that the invention is not limited to the precise arrangements shown.

DETAILED DESCRIPTION OF THE INVENTION

Specific embodiments of the present application will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Recitations of "at least one" component, element, etc. in the present disclosure and appended claims should not be used to create an inference that the alternative use of the articles "a" or "an" should be limited to a single component, element, etc.

In the present disclosure and appended claims, recitations of a component being "configured" to embody a particular property, or function in a particular manner, are structural recitations, as opposed to recitations of intended use. More specifically, references to the manner in which a component is "configured" denotes an existing physical condition of the component and, as such, is to be taken as a definite recitation of the structural characteristics of the component.

As used in the present disclosure and appended claims, terms like "preferably," "commonly," and "typically" are not utilized to limit the scope of the claims or to imply that certain features are critical, essential, or even important to the structure or function of the claimed embodiments. Rather, these terms are merely intended to identify particular aspects of an embodiment of the present disclosure or to emphasize alternative or additional features that may or may not be utilized in a particular embodiment of the present disclosure.

The terms "substantially" and "approximately," as used in the present disclosure and appended claims, represent the inherent degree of uncertainty that may be attributed to any quantitative comparison, value, measurement, or other representation. Such terms are also utilized to represent the degree by which a quantitative representation may vary from a stated reference without resulting in a change in the basic function of the subject matter at issue.

Unless otherwise indicated, all numbers expressing quantities, properties, conditions, and so forth as used in the specification and claims are to be understood as being modified in all instances by the term "about." Additionally, the disclosure of any ranges in the specification and claims are to be understood as including the range itself and also anything subsumed therein, as well as endpoints. Notwithstanding that numerical ranges and parameters setting forth the broad scope of the disclosure are approximations, the numerical values set forth in the specific examples are reported as precisely as possible. Any numerical values, however, inherently contain certain errors necessarily resulting from error found in their respective measurements.

"Automatically" includes the use of a machine to conduct a particular action. The process by which data is extracted, organized and stored is a data-driven and largely automatic process and may utilize a computer network (e.g., wide area network, such as the internet, a local area network, a mobile communications network, a public service telephone network, and/or any other network) and may be configured to electronically connect a user computing device (e.g., a PC) and a server computing device (e.g., cloud, mainframe, or other server device).

"Calculate" includes automatically determining or ascertaining a result.

"Computer" includes a machine (e.g., desktop, laptop, tablet, smartphone, television, server, as well as other current or future computer instantiations) containing a computer processor that has been specially configured with a set of computer executable instructions. References to "at least one" computer are intended to encompass both autonomous systems and sub-systems as well as situations where a given functionality might be divided across multiple machines (e.g. parallel processing) for efficiency or other purposes.

"Data Receiver" as used herein includes any component configured to receive data.

"Exemplary" as used herein means giving an example; serving as an illustration or example of something.

"GUI" or "Graphical User Interface" includes a user interface displayed on a visual subsystem (e.g., desktop monitor, tablet/phone screen, interactive television screen, etc.) by which users interact with electronic devices via images (e.g., lists, hyperlinks, panels, etc.).

"Parametric Mathematical Model" as used herein includes any mathematical model which can be described using a finite number of parameters.

A "Processor" may include any processing component configured to receive and execute instructions (such as from the data storage component and/or memory component). Network interface hardware may include any wired/wireless hardware generally known to those of skill in the art for communicating with other networks and/or devices.

"Root Mean Square," also known as the quadratic mean and abbreviated RMS, as used herein is a statistical measure of the magnitude of a varying quantity and is calculated as the square root of the arithmetic mean (average) of the squares of the original values.

A "Skin-Bone Complex" as used herein is bone and the overlying soft tissue including skin and muscle.

A "Server" may be specially configured or configured as a general purpose computer with the requisite hardware, software, and/or firmware. A server may include a processor, input/output hardware, network interface hardware, a data storage component (which stores data and/or metadata) and a memory component configured as volatile or non-volatile memory including RAM (e.g., SRAM, DRAM, and/or other types of random access memory), flash memory, registers, compact discs (CDs), digital versatile discs (DVD), and/or other types of storage components. A memory component may also include operating logic that, when executed, facilitates the operations described herein. An administrative computing device may also be employed to facilitate manual corrections to the metadata.

"Viscoelastic Material" as used herein includes material that has both damping and elastic properties.

In embodiments, a parametric model based computer implemented method for determining the stiffness of a bone is disclosed. Stiffness, as used herein, is the mechanical property measuring the resistance offered by an elastic body to deformation. It can be represented by $F/\delta$, wherein F is the force applied to the body and $\delta$ is the displacement produced by the force. In some embodiments, the computer implemented method utilizes improved Mechanical Response Tissue Analysis (MRTA) known as cortical bone mechanics technology (CBMT). In one or more embodiments, improved MRTA and CBMT involves a two-step technique for measuring the mechanical properties (i.e., mass, stiffness and damping) of long bones, such as the ulna in the human arm. The first step of improved MRTA and CBMT generally involves the collection of data in the form of a complex accelerance frequency response function, A(f). The second step of MRTA and improved CBMT generally involves the analysis of this complex accelerance frequency response function, A(f) by fitting A(f) to a parametric mathematical model of the skin-bone complex to estimate the values of mechanical properties thereof. The parametric mathematical model takes the form of a complex rational polynomial. The purpose of the disclosed embodiments is to facilitate the collection of a complex accelerance frequency response function, A(f) that conforms well to the parametric mathematical model.

With reference to FIGS. 2A-2D, in some embodiments, the first step of improved MRTA and CBMT involves collecting data in the form of a complex accelerance frequency response function, A(f) of a skin-bone complex. The skin-bone complex is bone and the overlying soft tissue including skin and muscle. In some embodiments, the complex accelerance frequency response function, A(f), data are collected by: (1) positioning a force probe on the skin overlying the bone, (2) applying both (i) a static force and (ii) oscillatory forces (F), (3) varying the frequency of the oscillatory forces (F) over a sub-range of the auditory frequency range, (4) measuring (i) the force applied through the force probe to the skin and (ii) the resulting acceleration of the force probe on the skin to obtain an oscillatory acceleration (a) of the skin-bone complex, and (5) calculating accelerance (i.e., acceleration divided by force) as a complex function of frequency, i.e., the complex accelerance frequency response function, A(f).

A "complex" function of frequency is one that records both (1) the magnitude of the oscillatory acceleration (a) that occurs in response to the applied oscillatory forces (F) relative to the magnitude of the oscillatory forces (F), and (2) the phase delay between the peak of the oscillatory forces (F) and the peak of the oscillatory acceleration (a). Mathematically equivalently, the magnitude and phase delay of a "complex" function of frequency may be expressed and recorded as a real part 26 and an imaginary part 24, wherein the real part 26 is equal to the magnitude multiplied by the cosine of the phase delay, and the imaginary part 24 is equal to the magnitude multiplied by the sine of the phase delay.

In some embodiments, the second step in improved MRTA and CBMT involves analysis of the complex accelerance frequency response function, A(f), to determine the mechanical properties of the bone. Such analysis includes fitting the complex accelerance frequency response function, A(f) to the parametric mathematical model. The parametric mathematical model represents the mechanical behavior of the skin-bone complex. Referring to FIG. 1, in one or more embodiments, the parametric mathematical model includes 7 parameters and accounts for the mass, stiffness, and damping of the skin and bone as well as parallel damping of soft tissues. Specifically, the 7-parameter model accounts for mass of the skin 8 ($M_S$), compressive stiffness of the skin 2 ($K_S$), damping coefficient of the skin 12 ($B_S$), mass of the bone 10 ($M_B$), transverse bending stiffness of the bone 6 ($K_B$), damping coefficient of the bone 14 ($B_B$), and damping coefficient of the surrounding soft tissue 4 ($B_P$). These parameters may alternatively be referenced using lowercase letters, e.g. ($m_s$), ($k_s$), ($b_s$), ($m_b$), ($k_b$), ($b_b$), and ($b_p$). While the present disclosure is applicable to numerous parametric mathematical models, for purposes of conveniently describing certain embodiments thereof, reference will be made to the 7-parameter model. However, one of skill in the art will recognize that reference to the 7-parameter model is not intended to be limiting and that the methods and systems disclosed herein may be applicable to alternate parametric mathematical models.

Integrating A(f) twice with respect to frequency yields a complex compliance frequency response function, Y(f)=x(f)/F(f) in which "x" is displacement. Inverting Y(f) yields the associated complex stiffness frequency response function, H(f)=F(f)/x(f).

The differential equations of motion representing the parametric mathematical model with 7-parameters are:

$$F - K_S(x_S - x_B) - B_S\left(\frac{dx_S}{dt} - \frac{dx_B}{dt}\right) - B_P\frac{dx_S}{dt} = M_S\frac{d^2 x_S}{dt^2}$$

$$K_S(x_S - x_B) - K_B x_B + B_S\left(\frac{dx_S}{dt} - \frac{dx_B}{dt}\right) - B_B\frac{dx_B}{dt} = M_B\frac{d^2 x_B}{dt^2}$$

As H(f)=Real{H(f)}+j Imag{H(f)}, wherein ω=2πf, H(f) can be determined in terms of things which are known and measurable. Specifically, $$\text{Real}\{H(\omega)\} = \frac{M_S[(C_0 - \omega^2)(\omega^4 - A_2\omega^2 + A_0) - C_1\omega(A_3\omega^3 - A_1\omega)]}{(C_0 - \omega^2)^2 + (C_1\omega)^2}$$

$$\text{Imag}\{H(\omega)\} = \frac{M_S[C_1\omega(\omega^4 - A_2\omega^2 + A_0) + (C_0 - \omega^2)(A_3\omega^3 - A_1\omega)]}{(C_0 - \omega^2)^2 + (C_1\omega)^2}$$

wherein, $$A_0 = \frac{K_S K_B}{M_S M_B}$$

$$A_1 = \frac{[K_B(B_S + B_P) + K_S(B_B + B_P)]}{M_S M_B}$$

$$A_2 = \frac{(K_S + K_B)}{M_B} + \frac{K_S}{M_S} + \frac{[B_S(B_B + B_P) + B_B B_P]}{M_S M_B}$$

$$A_3 = \frac{(B_S + B_P)}{M_B} + \frac{(B_S + B_P)}{M_S}$$

-continued $$C_1 = \frac{(B_S + B_B)}{M_B}$$

$$C_0 = \frac{(K_S + K_B)}{M_B}$$

Inverting the associated complex stiffness frequency response function, H(f), generates complex compliance frequency response function, Y(f).

Utilizing basic algebraic manipulation, the values for each of the 7 parameters can be determined from the fitted regression coefficients, $A_0$, $A_1$, $A_2$, $A_3$, $C_1$, and $C_0$. In embodiments, the determination of each of the 7 parameters is independently made from Y(f) and from H(f).

Those who practiced MRTA as it was originally conceived used the RMS of deviations of force/displacement data collected from a limb to the mathematical model of the mechanical skin-bone system. In so doing they trusted that the method of least squares analysis is quite robust in that small or minor violations of the underlying assumptions do not invalidate the inferences or conclusions drawn from the analysis in a major way and overlooked the fact that gross violations of the model assumptions can, however, seriously distort conclusions. Indeed, in this prior practice of MRTA, reliance upon the method of least squares often yielded widely discrepant estimates of $K_B$ from multiple parameter sets collected from the same limb, even when the requirement for an acceptable fit was an RMS error of less than 10%.

Indeed, a gross violation of model assumptions commonly occurs when an unmodeled mode of vibration is present in frequency response function data. This condition can have negligible and indistinguishable effects on the RMS of deviations of data points from the model, (e.g., $R^2$=0.997 to 0.999) even though values of $K_B$ vary greatly (e.g., $K_B$=35.7 to 83.3 $Nm^2$). Under such conditions, however, the values of the RMS of differences between parameter estimates from fits to stiffness and compliance forms of the frequency response function data also vary widely and are easily distinguished (e.g., RMS=3.7% to 82.5%).

Thus, in theory, data conforming perfectly to the 7-parameter model, fitting the 7-parameter model to Y(f) and H(f) should yield exactly the same values for each of the 7 parameters. However, in practice the values of the 7 parameters vary between those obtained from Y(f) and those obtained from H(f), and the extent to which these values of the 7 parameters differ from one another is a measure of the extent to which the data do not conform to the 7-parameter model.

In embodiments, the static force applied to the skin overlying the bone serves at least two functions. As approximated by the 7-parameter model of the skin-bone complex of the forearm, the skin-bone complex has two resonances, the properties of which are determined primarily, but not entirely, by the bone in one case and by the skin and other soft tissue between the surface of the skin and the bone in the other case. The first function of the static load is to exceed the amplitude of the oscillatory forces (F), so that the force probe does not separate from the arm on every negative phase of the oscillatory forces (F). The second function of the static load is to compress the soft tissue overlying the ulna, squeezing tissue fluid out from between the surface of the skin and the underlying bone, thereby increasing the stiffness and reducing the mass of this tissue. Because the resonant frequency of a mechanical system is proportional to the square root of the system's effective stiffness divided by its effective mass, increasing the static load increases the frequency of the resonance associated with the skin, separating it from the resonance associated with the ulna, and thereby improving the ability to more accurately estimate the mechanical properties of the bone and skin. The magnitude of the static load that optimizes these estimates varies with individual differences in the amount of soft tissue between the surface of the skin and the underlying ulna, and is best determined by iteratively collecting and analyzing data, and adjusting the static load in such a manner as to maximize conformity of the data to the 7-parameter model. In various embodiments, the static load varies between approximately 3 N and approximately 30 N. Static loads lower than approximately 3 N are generally insufficient, even in lean patients and static loads greater than approximately 30 N are painful, even in obese or muscular people. In other embodiments the range of static loads varies within a subrange of approximately 3 N and approximately 30 N, such as between approximately 3 N and approximately 25 N, between approximately 5 N and approximately 30 N or, between approximately 10 N and approximately 20 N.

In embodiments of a parametric model based computer implemented method for determining the stiffness of a bone, the method initially comprises applying a superposition of static and oscillatory forces (F) over a range of frequencies (f), i.e. vibrations, to a region of the skin-bone complex of a bone of interest, e.g., the ulna. The oscillatory forces (F) applied to the skin-bone complex induce corresponding oscillatory accelerations (a) over the range of frequencies (f) of the skin-bone complex. Further, a data receiver receives measurement of the oscillatory forces as functions of time F(t) and the resulting oscillatory accelerations (a) as functions of time a(t). The data receiver is communicatively coupled to a controller. Communicatively coupled means electrically, signally, wirelessly, wired, optically, or similarly connected. The controller comprises a processor and a storage medium containing computer readable and executable instructions which, when executed by the processor, cause the controller to automatically execute a series of analysis steps to determine the stiffness of the bone based on the measured oscillatory forces as functions of time F(t) and the resulting oscillatory accelerations as functions of time a(t).

With reference to FIGS. 3 and 4, the controller, in accordance with the executable instructions on the storage medium containing computer readable and executable instructions, automatically determines the oscillatory acceleration (a) and oscillatory forces (F) as functions of frequency, a(f) and F(f) respectively by performing Fourier transformations to convert a(t) and F(t) to a(f) and F(f) respectively. Additionally, the controller automatically determines the complex compliance frequency response function, Y(f) and the associated complex stiffness frequency response function H(f). In embodiments Y(f) and H(f) are determined by reducing a(f) and F(f) to the complex accelerance frequency response function A(f) and integrating A(f) twice in accordance with the mathematical manipulation previously discussed. Additionally, the controller automatically fits a parametric mathematical model to Y(f) to obtain a first complete and fully converged set of parameters of the parametric mathematical model, including the stiffness of the bone ($K_B$), as well as fits the parametric mathematical model to H(f) to obtain a second complete and fully converged set of parameters of the parametric mathematical model, including the stiffness of the bone ($K_B$). The parametric mathematical model may also be as previously discussed.

The parametric mathematic model of the complex compliance frequency response function is characterized by two resonant peaks. One of these peaks is determined primarily by the mechanical properties of the skin such as the mass, the stiffness, and the damping of the skin. This characteristic peak is the skin peak 22 and appears between approximately 600 and 800 Hz in FIGS. 2 and 3. The other characteristic peak is determined primarily by the mechanical properties of the underlying ulna bone and is the bone peak 20. The bone peak 20 appears between approximately 200 and 250 Hz in FIGS. 2 and 3. The form of the bone peak 20 is a sensitive function of various factors including the location of probe placement on the forearm in MRTA or CBMT data collection. Determination of the correct location for probe placement on the forearm is not achievable by sight or touch so determination of correct placement must be determined from analysis of collected data. Misplacement of the probe causes distortion of the bone peak 20 and errors in measurements of $K_B$ so determination of bone peaks 20 without distortion allows for selection of measurements with a correct probe placement.

FIGS. 2A-2D, 3A-3D, and 4A-4D each include both the imaginary part 24 and the real part 26 of each of A(f), Y(f), and H(f) respectively. In addition to a plot of the imaginary part 24 and the real part 26 of the frequency response function data, each figure also includes compliance and stiffness data of the best fit superimposed on the frequency response function data. Specifically, FIGS. 2A-2D include the fit to the compliance frequency response function differentiated twice and superimposed on the accelerance frequency response function 72 as well as the fit to the stiffness frequency response function inverted, differentiated twice, and superimposed on the accelerance frequency response function data 73. Similarly, FIGS. 3A-3D include the fit to the compliance frequency response function 74 as well as the fit to the stiffness frequency response function inverted and superimposed on the compliance frequency response function data 75. Finally, FIGS. 4A-4D include the fit to the stiffness frequency response function 76 as well as the fit to the compliance frequency response function inverted and superimposed on the stiffness frequency response function data 77.

In embodiments of a parametric model based computer implemented method for determining the stiffness of a bone, the controller further automatically determines discrepancies between the first complete and fully converged set of parameters and the second complete and fully converged set of parameters as a first measure of conformity thereof to the parametric mathematical model.

In embodiments of a parametric model based computer implemented method for determining the stiffness of a bone, the controller further automatically determines a second measure of conformity. The second measure of conformity reflects the agreement between the bone peak in the complex compliance frequency response function and the bone peak in the parametric mathematical model. The comparison of the complex compliance frequency response function and the parametric mathematical model may be achieved by comparing the skewness and the kurtosis of the bone peaks in each respectively. A higher degree of conformity between the shape of the bone peaks in the complex compliance frequency response function and the parametric mathematical model as reflected by measurement of their skewness and their kurtosis is indicative of a higher degree of conformity between the collected data set and the patient's true bone properties.

Skewness is a measure of the asymmetry of the data around the sample mean. If skewness is negative, the data are spread out more to the left of the mean than to the right. If skewness is positive, the data are spread out more to the right. The skewness of the normal distribution (or any perfectly symmetric distribution) is zero. As the asymmetry increases the magnitude of skewness increases.

The skewness of a distribution is defined as $$S = \frac{E(x-\mu)^3}{\sigma^3}$$

where $\mu$ is the mean of x, $\sigma$ is the standard deviation of x, and E(t) represents the expected value of the quantity t.

When applied to an inherently biased sample of data from a population, skewness may be calculated by the following computational formula:

$$S = \frac{\sqrt{n(n-1)}}{n-2} \times \frac{\left(\frac{1}{n}\right)\sum_{i=1}^{n}(x_i-\bar{x})^3}{\left[\left(\frac{1}{n}\right)\sum_{i=1}^{n}(x_i-\bar{x})^2\right]^{\frac{3}{2}}}$$

Kurtosis is a measure of how spread out a graphical peak is providing a relation between the height and the width. A graphical peak with short tails and the distribution tightly clustered to the center would have a small kurtosis where a graphical peak with long tails and the distribution spread out away from the center would have a greater kurtosis. The kurtosis of a normal distribution is 3. More spread out distributions have kurtosis greater than 3, and less spread out distributions have kurtosis less than 3.

The kurtosis of a distribution is defined as $$K = \frac{E(x-\mu)^4}{\sigma^4}$$

where $\mu$ is the mean of x, $\sigma$ is the standard deviation of x, and E(t) represents the expected value of the quantity t.

When applied to an inherently biased sample of data from a population, kurtosis may be calculated by the following computational formula:

$$K = \frac{n-1}{(n-2)(n-3)} \times \left((n+1)\frac{\left(\frac{1}{n}\right)\sum_{i=1}^{n}(x_i-\bar{x})^4}{\left[\left(\frac{1}{n}\right)\sum_{i=1}^{n}(x_i-\bar{x})^2\right]^{2}} - 3(n-1)\right) + 3$$

The second measure of conformity is derived from the computed values of skewness (S) and kurtosis (K). In one or more embodiments, first, a bone peak skewness error ($E_S$) is calculated by subtracting from S the skewness of the bone peak in a perfect 7-parameter model ($S_0$=1.37): $E_S$=S−$S_0$. Then, a bone peak kurtosis error ($E_K$) is calculated by subtracting from K the kurtosis of the bone peak in a perfect 7-parameter model ($K_0$=3.17): $E_K$=K−$K_0$. The second measure of conformity may be obtained as an arithmetic combination of the bone peak skewness error and the bone peak kurtosis error. In one or more embodiments, the total bone peak skewness and kurtosis error is calculated by adding the absolute values of these two errors: SnK=|$E_S$|+|$E_K$| as the second measure of conformity (Skewness and Kurtosis Error).

The controller saves the first measure of conformity, the first complete and fully converged set of parameters, the second complete and fully converged set of parameters, and the second measure of conformity as a parameter set.

As shown in FIGS. 2, 3, and 4, when the first and second measures of conformity indicate a good fit, the fit parametric mathematical model conforms to the collected data closely. Specifically, between approximately 150 Hz and 725 Hz, the fit parametric mathematical model can be seen graphically overlaid over the empirical A(f), Y(f), and H(f) in FIG. 2, FIG. 3, and FIG. 4 respectively. Additionally, both the imaginary part 24 and the real part 26 of each of A(f), Y(f), and H(f) are shown. Each of the parameter sets provides acceptable results in accordance with the first measure of conformity. Once the second measure of conformity accounting for the skewness and kurtosis of the bone peaks in each data set is considered the distinction between the optimal parameter sets in FIGS. 2A, 3A, 4A, 2C, 3C, and 4C and the sub-optimum data sets in FIGS. 2B, 3B, 4B, 2D, 3D, and 4D is highlighted.

The second measure of conformity provides improved selection of the optimal parameter set for utilization in final bone mechanical property determination. Specifically, solely evaluating the first measure of conformity may yield more than 1 parameter set that satisfies that selection criterion. However, each parameter set yields a different and distinct stiffness value. It is beneficial to be able to further refine the parameter set selection such that the selected parameter set more closely reflects the bone stiffness value that would be measured by the widely accepted gold standard Quasistatic Mechanical Testing (QMT) method. The addition of the second measure of conformity allows the selection of the optimized parameter set to be further refined to distinguish between multiple parameter sets which appear acceptable based on solely the first measure of conformity.

With both the first measure of conformity and the second measure of conformity, the accuracy and repeatability of improved MRTA and CBMT measurements are improved in an objective and quantitative manner. Specifically, the accuracy or closeness of the calculated $K_B$ to a measurement that would be obtained by QMT is improved as a $K_B$ is obtained from a parameter set that more closely matches this value. Additionally, improved repeatability is achieved as the coefficient of variation of repeated measurements in the same person is reduced from the improvement in selecting which of multiple parameter sets for utilization in final $K_B$ determination. For example, the frequency response function parameter sets from a cadaveric human arm illustrated in FIGS. 2A-2B were two of four parameter sets that satisfied the first measure of conformity in experimental testing. The coefficient of variation of the four measurements derived from those four parameter sets was 5%. Of those four parameter sets, only two also satisfied the second measure of conformity. The coefficient of variation of the measurements derived from those two parameter sets was 1%. Finally, the accuracy and repeatability of improved MRTA and CBMT measurements are improved in an objective manner as the selection of the optimized parameter set is based on quantitative algorithmic methods which remove human selection bias from the determination decision.

In various embodiments the saving of the first measure of conformity, the first complete and fully converged set of parameters, the second complete and fully converged set of parameters, and the second measure of conformity as a parameter set is completed using the storage medium. In some embodiments every parameter set generated is saved and retained in the storage medium. In further embodiments, only a predetermined number of parameter sets are retained in the storage medium and as new parameter sets are generated the oldest parameter sets are deleted and/or written over. In still further embodiments, in lieu of, or in addition to, saving the parameter sets to the storage medium the parameter sets are physically printed such that hard copies of the first and second measures of conformity, the first complete and fully converged set of parameters, and the complete and fully converged second set of parameters in each parameter set are generated. In yet further embodiments, the parameter sets are saved on a storage medium located in a server external to the system.

In other embodiments the parameter set also includes a record of Y(f), H(f), or Y(f) and H(f). Retaining the raw data representing Y(f) and/or H(f) allows repeated or alternative analysis to be performed at a later time.

Further, in an effort to obtain an optimized parameter set, the static and oscillatory forces (F) are applied to a shifted region of the skin-bone complex and the data receiver receives measurement of the oscillatory forces as functions of time F(t) and the resulting oscillatory accelerations (a) as functions of time a(t). for the shifted region. The controller, in accordance with the executable instructions on the storage medium containing computer readable and executable instructions, automatically determines the oscillatory acceleration (a) and oscillatory forces (F) as functions of frequency, a(f) and F(f) respectively by performing Fourier transformations to convert a(t) and F(t) to a(f) and F(f) respectively for the shifted region. Additionally, the controller automatically determines the complex compliance frequency response function, Y(f) and the associated complex stiffness frequency response function H(f) for the shifted region. In embodiments Y(f) and H(f) are determined by reducing a(f) and F(f) to the complex accelerance frequency response function A(f) and integrating A(f) twice in accordance with the mathematical manipulation previously discussed. Additionally, the controller automatically fits the parametric mathematical model once again to the Y(f) to obtain a new iteration of the first complete and fully converged set of parameters of the parametric mathematical model, including the stiffness of the bone ($K_B$), as well as fits the parametric mathematical model to H(f) to obtain a new iteration of the second complete and fully converged set of parameters of the parametric mathematical model, including the stiffness of the bone ($K_B$). Repetition of collection of the oscillatory forces (F) and the resulting oscillatory accelerations (a) for shifted regions and analysis of the collected oscillatory forces (F) and oscillatory accelerations (a) to determine parameters of the parametric mathematical model is continued until the optimized parameter set is determined.

In various embodiments the static force applied to the skin-bone complex is adjusted for some or all repetitions of collection of the oscillatory forces (F) and the resulting oscillatory accelerations (a) for the shifted regions.

In various embodiments one or more layers of a viscoelastic material is applied over the skin-bone complex. In other embodiments one or more layers of a viscoelastic material is applied under the skin-bone complex between the skin-bone complex and the structure upon which the skin-bone complex rests. In still other embodiments one or more layers of a viscoelastic material is applied both over the skin-bone complex and between the skin-bone complex and the structure upon which the skin-bone complex rests.

In an embodiment, the optimized parameter set is determined based on the first and second measures of conformity. The optimized parameter set may also be iteratively determined by systematically reducing the first measure of conformity and the second measure of conformity. If, when the superposition of static and oscillatory forces (F) over a range of frequencies (f) are applied to a shifted region of the skin-bone complex the first measure of conformity of the first complete and fully converged set of parameters and the second complete and fully converged set of parameters is improved, the first complete and fully converged set of parameters and the second complete and fully converged set of parameters of the shifted region are believed to represent an improved representation of the true parameters of the bone over the previous sets of parameters. An improved first measure of conformity would represent a lower value with the discrepancy between the first complete and fully converged set of parameters and the second complete and fully converged set of parameters reduced. The repetition of collection of the oscillatory forces (F) and the resulting oscillatory accelerations (a) for shifted regions and analysis of the collected oscillatory forces (F) and oscillatory accelerations (a) to determine parameters of the parametric mathematical model is continued until the first measure of conformity is worsened. The worsening of the first measure of conformity indicates the shifted region has traversed past the ideal region of the bone for data collection and the optimized parameter set is the immediately previously collected first complete and fully converged set of parameters and second complete and fully converged set of parameters. Similarly, the second measure of conformity may be monitored with the worsening of the second measure of conformity indicating misplacement of the shifted region for data collection.

In shifting the bone probe to collect data at a shifted region, the superposition of static and oscillatory forces (F) over a range of frequencies (f) may be initially applied to a region of the skin-bone complex medial of the centerline of the ulna, then the static and oscillatory forces (F) over a range of frequencies (f) are applied to a shifted region lateral of the initial region of the skin-bone complex, then the static and oscillatory forces (F) over a range of frequencies (f) are applied to a further shifted region further lateral of the initial region of the skin-bone complex. The first measure of conformity and the second measure of conformity improves upon each further lateral shift of the application of the static and oscillatory forces (F) until the optimum location for data collection is passed by. When the optimum location for data collection is passed by, the first and second measures of conformity will worsen. The optimized parameter set with respect to medial to lateral shifting of the region is represented by the saved parameter sets with the best first and second measures of conformity.

In other embodiments, a superposition of static and oscillatory forces (F) over a range of frequencies (f) are initially applied to a region of the skin-bone complex with the forearm at a particular angle of rotation with respect to its long axis, then static and oscillatory forces (F) over a range of frequencies (f) are applied to a region accessed by rotating the forearm on its long axis. The first and second measures of conformity improve upon each further rotational shift of the application of the static and oscillatory forces (F) until the optimum location for data collection is passed by. When the optimum location for data collection is passed by, the first and second measures of conformity will worsen. The optimized parameter set with respect to rotational shifting of the region is represented by the saved parameter set with the best first and second measures of conformity. Analogously, the region may be shifted longitudinally along the long axis of the forearm and an optimized parameter set with respect to longitudinal shifting of the region may be obtained.

Furthermore, the magnitude of the static load, and thereby the position of the resonance determined primarily by the mechanical properties of the skin and soft tissues, may be varied and an optimized parameter set with respect to static load obtained. In addition, layers of viscoelastic material may be inserted between the skin and the force probe that applies force to the skin, and an optimized parameter set with respect to the number of layers obtained. In this way an overall optimized parameter set is identified.

In one or more embodiments, the optimized parameter set is determined with the first measure of conformity below a predetermined first threshold value and the second measure of conformity below a predetermined second threshold value. As the first measure of conformity represents the discrepancy between the first complete and fully converged set of parameters and the second complete and fully converged set of parameters in the simultaneous fits of the parametric mathematical model to the complex stiffness and compliance frequency response functions, and as the second measure of conformity represents disagreement between the shapes of the bone peaks in the complex compliance frequency response function and the parametric mathematical model, minimizing the first and second measures of conformity corresponds to further agreement between the collected and model data.

Upon determination of the overall optimized parameter set, the stiffness of the bone can be determined. Additionally, in various embodiments, each of the individual optimized parameter sets may be used to determine the stiffness of the bone. Transverse bending stiffness of the bone ($K_B$) can be determined directly from the parametric parameters associated with the optimized parameter set. In embodiments, the determined stiffness of the bone is the transverse bending stiffness of the bone ($K_B$) generated from Y(f) as part of the first complete and fully converged set of parameters associated with the optimized parameter set. In other embodiments, the determined stiffness of the bone is the transverse bending stiffness of the bone ($K_B$) generated from H(f) as part of the second complete and fully converged set of parameters associated with the optimized parameter set. In still other embodiments, the determined stiffness of the bone is an average of the transverse bending stiffness of the bone ($K_B$) generated from Y(f) as part of the first complete and fully converged set of parameters associated with the optimized parameter set and the transverse bending stiffness of the bone ($K_B$) generated from H(f) as part of the second complete and fully converged set of parameters associated with the optimized parameter set. In yet still other embodiments, the determined stiffness of the bone is a weighted average of the transverse bending stiffness of the bone ($K_B$) generated from Y(f) as part of the first complete and fully converged set of parameters associated with the optimized parameter set and the transverse bending stiffness of the bone ($K_B$) generated from H(f) as part of the second complete and fully converged set of parameters associated with the optimized parameter set.

Additionally, in multiple embodiments, the determined stiffness of bone in the method is flexural rigidity, EI, and may be calculated based on the determined transverse bending stiffness 6 ($K_B$) of the bone. Specifically, $EI=K_B L^3/48$, wherein L is the length of the bone.

In various embodiments, the first measure of conformity between the first set of parameters and the second set of parameters is quantified as a root mean square (RMS) therebetween of the percentage differences between the seven parameters estimated from Y(f) and H(f), i.e. percentage root mean square (% RMS).

In various embodiments, the second measure of conformity is the sum of the absolute differences between the skewness of the bone peak in the complex frequency response function and the characteristic value of the skewness of the bone peak in the parametric mathematical model and between the kurtosis of the bone peak in the complex frequency response function and the characteristic value of the kurtosis of the bone peak in the parametric mathematical model.

Figure 2A:
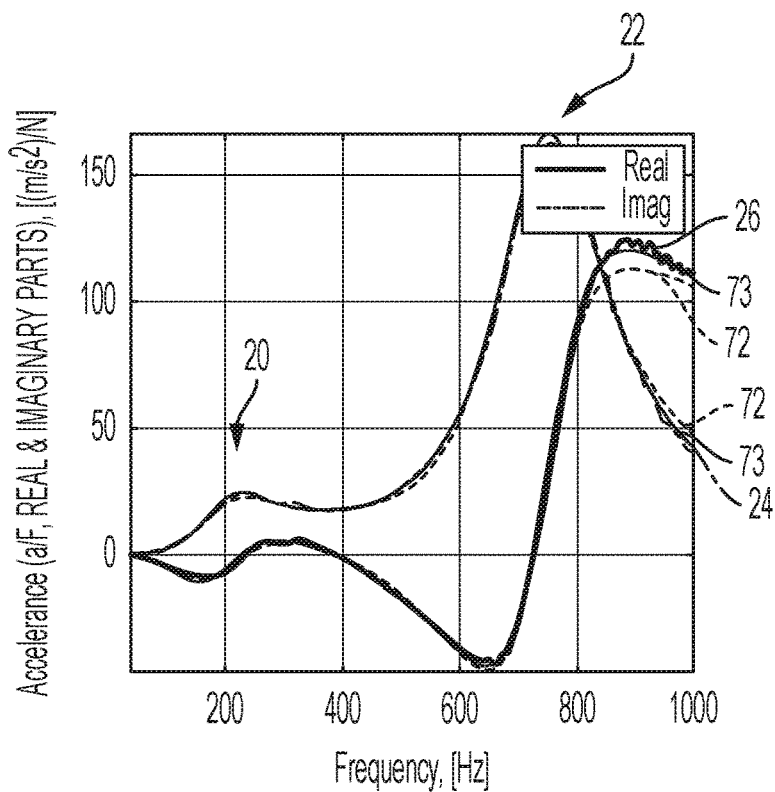
FIGS. 2A and 2B depict accelerance frequency response function data A(f) and the parametric mathematical model best fit of a cadaveric ulna specimen providing optimum and sub-optimum results respectively.
Figure 2B:
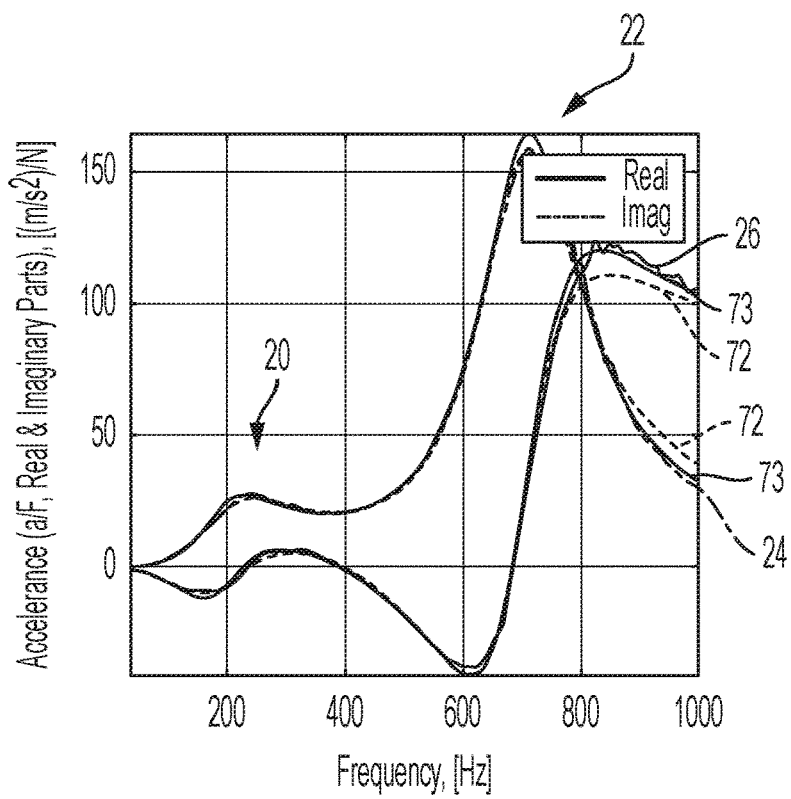
Figure 2C:
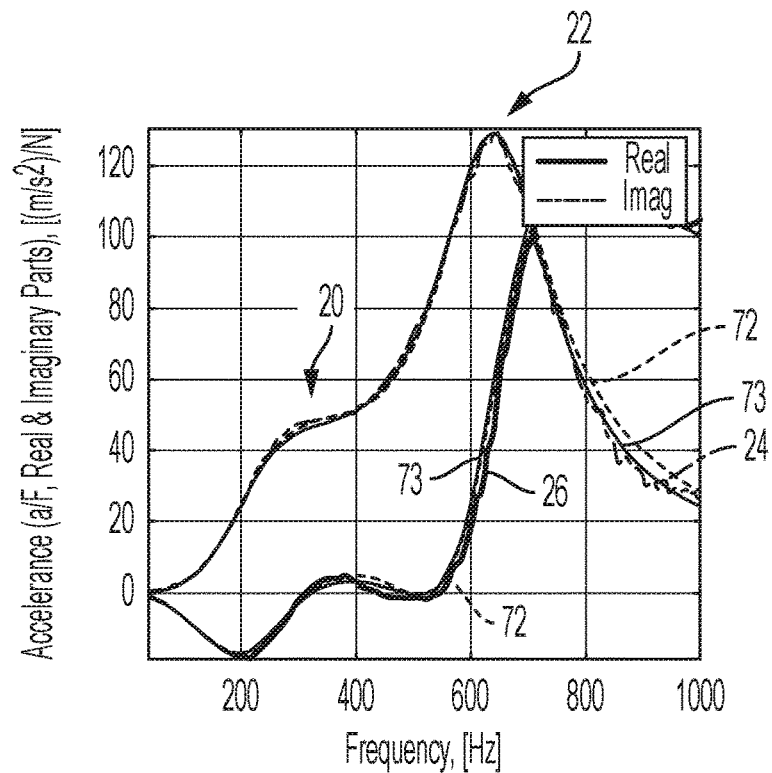
FIGS. 2C and 2D depict accelerance frequency response function data A(f) and the parametric mathematical model best fit of an in-vivo human ulna providing optimum and sub-optimum results respectively.
Figure 2D:
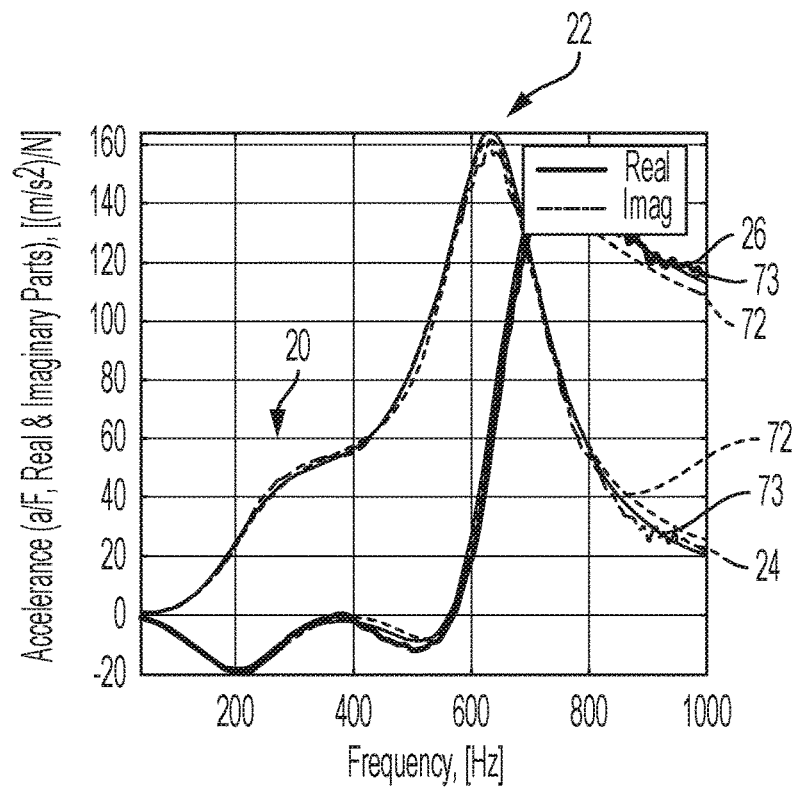
Figure 3A:
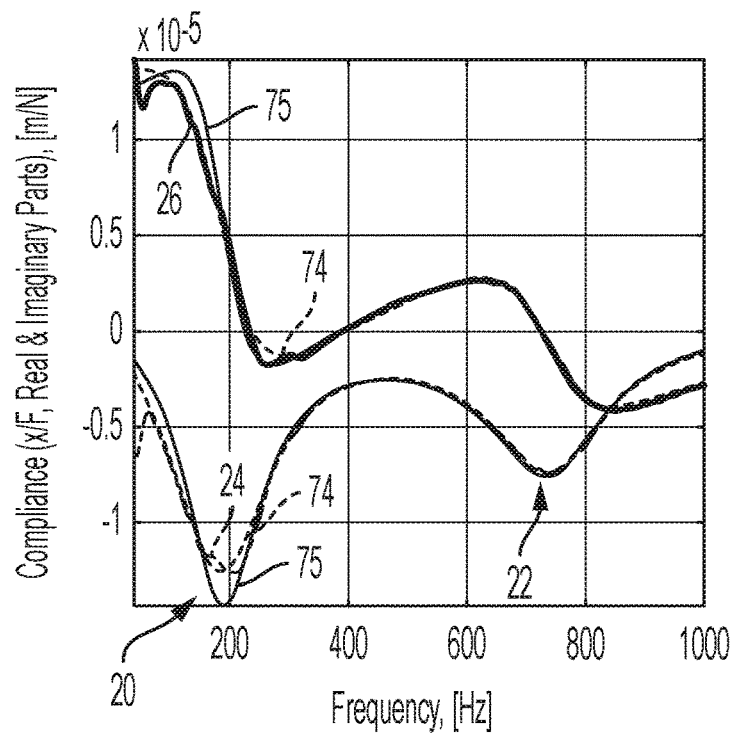
FIGS. 3A and 3B depicts complex compliance frequency response function Y(f) and the parametric mathematical model best fit of a cadaveric ulna specimen providing optimum and sub-optimum results respectively.
Figure 3B:
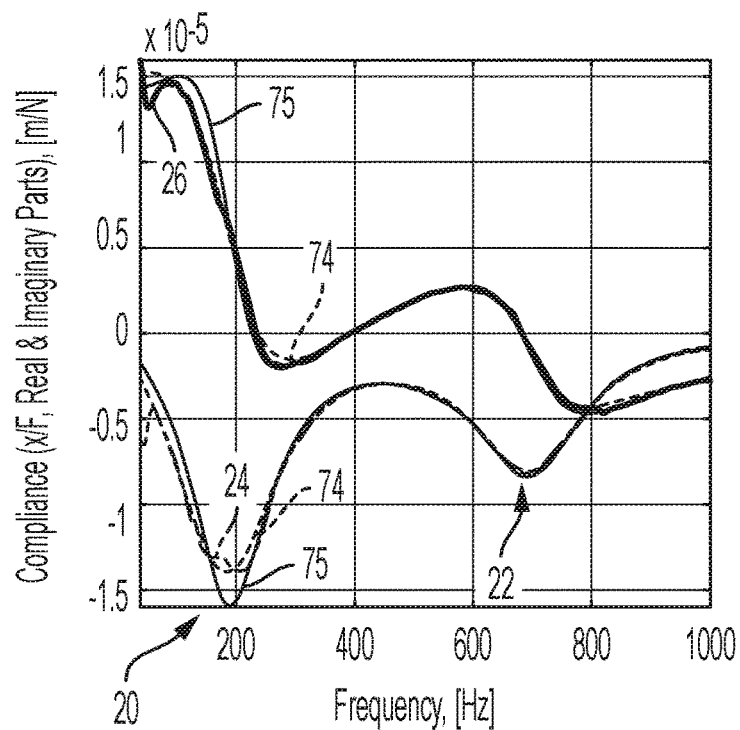
Figure 3C:
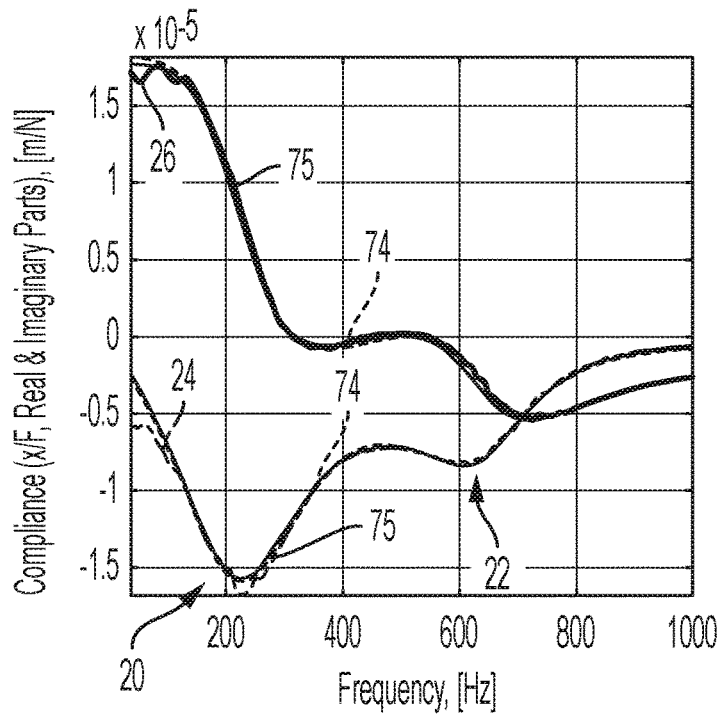
FIGS. 3C and 3D depicts complex compliance frequency response function Y(f) and the parametric mathematical model best fit of an in-vivo human ulna providing optimum and sub-optimum results respectively.
Figure 3D:
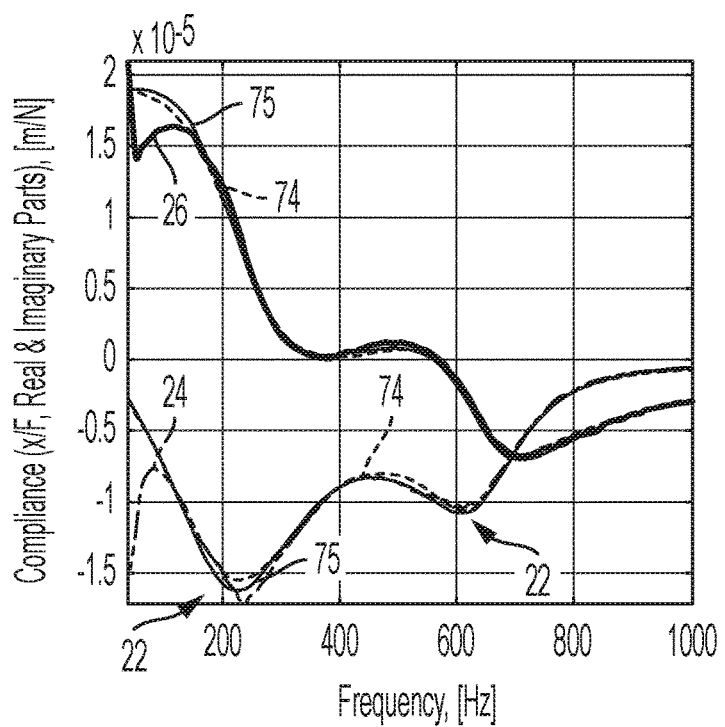
Figure 4A:
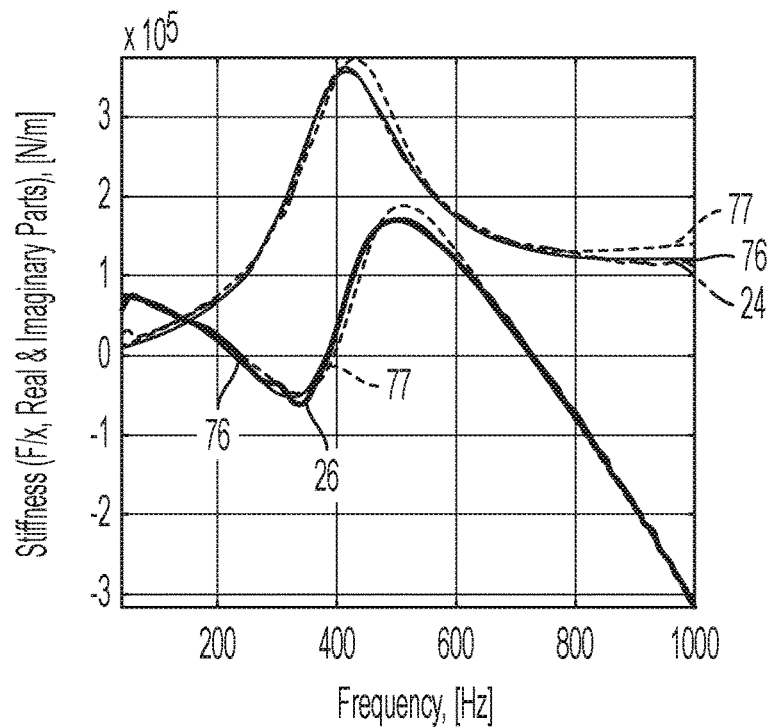
FIGS. 4A and 4B depicts complex stiffness frequency response function H(f) and the parametric mathematical model best fit of a cadaveric ulna specimen providing optimum and sub-optimum results respectively.
Figure 4B:
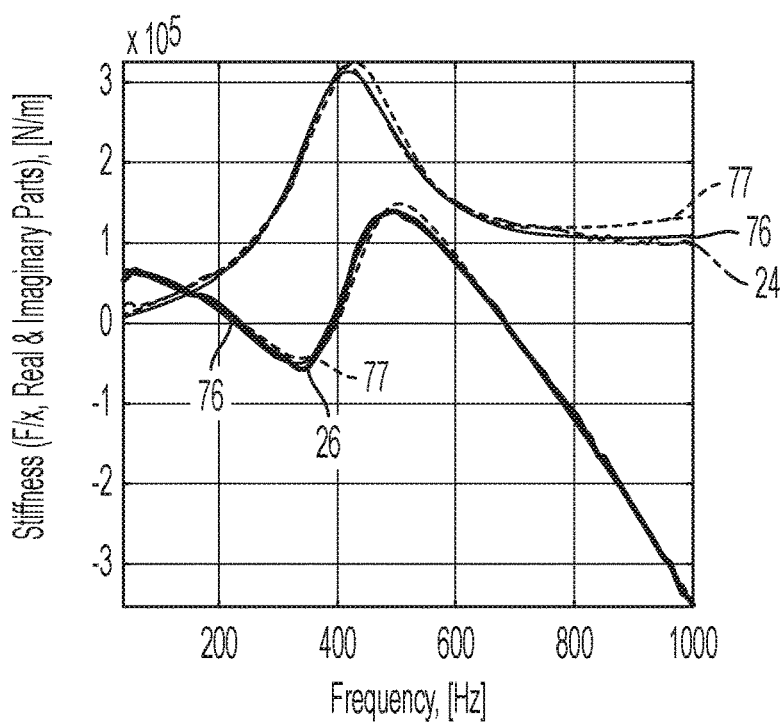
Figure 4C:
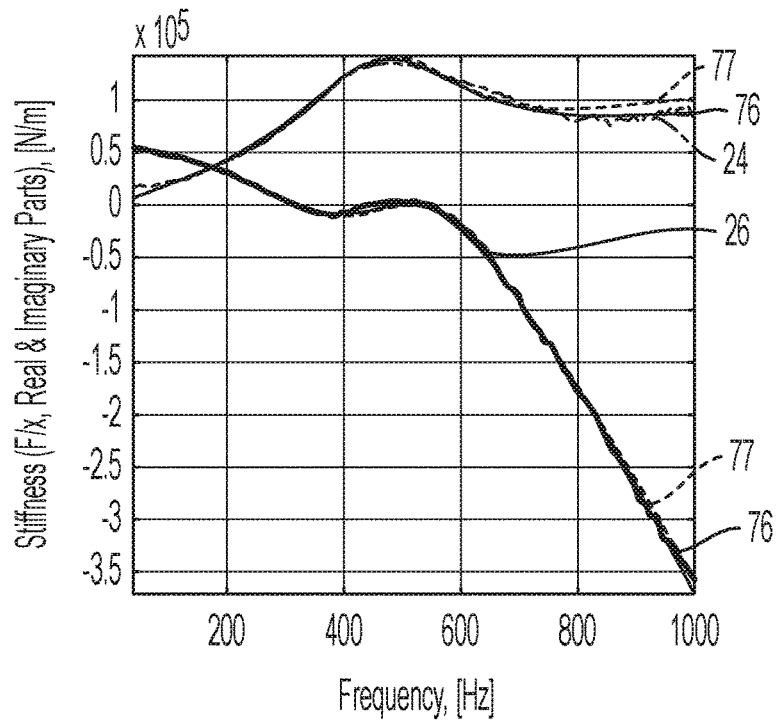
FIGS. 4C and 4D depicts complex stiffness frequency response function H(f) and the parametric mathematical model best fit of an in-vivo human ulna providing optimum and sub-optimum results respectively.
Figure 4D:
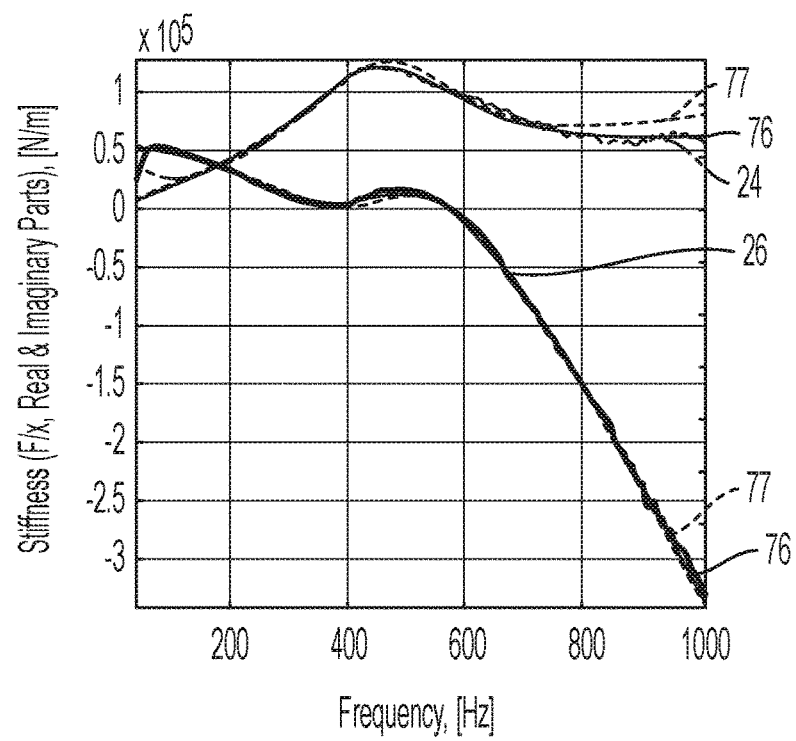

In one or more embodiments threshold values are set for the first measure of conformity and the second measure of conformity. The threshold value for the first measure of conformity may be a selection criterion of the root mean square below a cut-off value. For example, in various embodiments the threshold value for the first measure of conformity may be a root mean square less than 12%, less than 10%, less than 9%, less than 5%, or less than 3%. The threshold value for the second measure of conformity may be a selection criterion of the skewness and kurtosis error of below a cut-off value. For example, in various embodiments the threshold value for the second measure of conformity may be a Skewness and Kurtosis error of less than 0.250, less than 0.200, less than 0.195, or less than 0.180. For the frequency response function data analyzed in FIGS. 2A-4D threshold values of less than 9.0% (root mean square cut-off) and less than 0.195 (Skewness and Kurtosis Error cut-off) were utilized in determining optimal and sub-optimal frequency response functions. Optimal cadaveric data illustrated in FIGS. 2A, 3A, and 4A presented a root mean square of 2.2% and a Skewness and Kurtosis Error of 0.17 compared to values of 2.4% and 0.63 respectively for sub-optimal cadaveric data in FIGS. 2B, 3B, and 4B. Similarly, optimal in-vivo data illustrated in FIGS. 2C, 3C, and 4C presented a root mean square of 2.3% and a Skewness and Kurtosis Error of 0.06 compared to values of 1.5% and 0.32 respectively for sub-optimal in-vivo data in FIGS. 2D, 3D, and 4D.

In one or more embodiments, determination of a final stiffness value may be the result of calculation of the average of results from all parameter sets that satisfy both the first measure of conformity and the second measure of conformity. In further embodiments, if no parameter set is obtained which satisfied both the first measure of conformity and the second measure of conformity, the single parameter set satisfying the first measure of conformity that has the lowest second measure of conformity is selected.

Additionally, in accordance with the 7-parameter model, each of the parameters must have a positive value in the optimized parameter set. Specifically, mass of the skin 8 ($M_S$), transverse bending stiffness of the skin 2 ($K_S$), damping coefficient of the skin 12 ($B_S$), mass of the bone 10 ($M_B$), transverse bending stiffness of the bone 6 ($K_B$), damping coefficient of the bone 14 ($B_B$), and damping coefficient of the surrounding soft tissue 4 ($B_P$) are all by definition positive values. Thus, in embodiments, if the first complete and fully converged set of parameters or the second complete and fully converged set of parameters include a negative parameter value it is known that the sets of parameters are not ideal and thus do not represent the optimized parameter set.

It will be appreciated that a 6-parameter model in which damping coefficient of the surrounding soft tissue 4 ($B_P$) is absent from the 7-parameter model may be utilized for fitting data from ulna bones excised from cadaveric human arms. Exclusion of $B_P$ is necessary as there is no peripheral tissue around an excised ulna. While utilization of a 6-parameter model may have no or minimal commercial value for clinical purposes, it does provide substantial value for research purposes. Specifically, the transverse bending stiffness of the bone 6 ($K_B$) of an excised bone can be readily measured by QMT, but damping coefficient of the bone 14 ($B_B$) cannot. Therefore, bone researchers may want to use CBMT to test excised ulnas in order to obtain measurements of $B_B$.

Further, with reference to FIGS. 3A-3D, the area under the imaginary part of the compliance curve between 40 Hz and 100 Hz is preferably less than $6 \times 10^{-4}$ m/Ns. In the 7-parameter model, the imaginary part of compliance approaches zero as frequency approaches zero. If the subrange of frequency that minimizes % RMS does not include frequencies below 100 Hz, then departure from this feature of the 7-parameter model will not be detected by % RMS alone. Therefore, for greater confidence in conformity to the 7-parameter model, the area under the imaginary part of the compliance curve between 40 Hz and 100 Hz should be substantially less than approximately $6 \times 10^{-4}$ m/Ns=$1 \times 10^{-5}$ m/N×60 Hz. If the imaginary part of compliance does not satisfy this criterion the collected data are believed to be suboptimal.

In further embodiments, the oscillatory forces (F) are applied to the skin-bone complex through an excitation frequency range. In embodiments, the excitation frequency range has a minimum frequency of approximately 40 Hz and a maximum frequency of approximately 1200 Hz. In further embodiments, the excitation frequency range has a minimum frequency of approximately 80 Hz and a maximum frequency of approximately 1100 Hz. In still further embodiments, the excitation frequency range has a minimum frequency of approximately 100 Hz and a maximum frequency of approximately 1000 Hz.

In various embodiments, the excitation frequency range is selected such that the lower end or minimum frequency of the excitation frequency range is substantially less than the frequency of the bone peak 20 resonance frequency in the imaginary part 24 of the compliance frequency response function, and the upper end or maximum frequency of the excitation frequency range is substantially above the frequency of the skin peak 22 resonance frequency in the imaginary part 24 of the compliance frequency response function.

In various embodiments, the oscillatory forces (F) are applied over the excitation frequency range in a swept sine waveform, a pseudorandom waveform, a uniform random waveform, a shaped random waveform, a chirp waveform, a burst waveform, a burst random waveform, a shaped burst random waveform, a white noise waveform, a pink noise waveform, or other standard waveforms known to one of ordinary skill in the art.

In various embodiments, the parametric mathematical model is fit to Y(f) and H(f) at a plurality of subranges within the excitation frequency range. In theory, for data conforming perfectly to the 7-parameter model, fitting the 7-parameter model to either Y(f) or H(f) should yield exactly the same estimates of the 7 parameters regardless of the frequency range over which the model is fitted; however, in practice it does not. Fitting the parametric mathematical model at a plurality of subranges produces a plurality of first and second sets of parameters and thus the subrange with the best measure of conformity for the first and second set of parameters may be selected. Specifically, in embodiments, the controller fits the 7-parameter model to both Y(f) and H(f) over a large number of frequency subranges with varying low starting frequencies, i.e., minimum frequencies, and varying high ending frequencies, i.e., maximum frequencies. Fitting the 7-parameter model to both Y(f) and H(f) produces a plurality of first and second sets of parameters. The controller then instructs the processor to calculate the percentage root mean square of the differences between the first and second sets of parameters for each frequency subrange and reports the minimum percentage root mean square as a measure of the extent to which A(f) departs from the form of the 7-parameter model. It will be appreciated that 10s, 100s, or 1000s of individual measurements at distinct frequency ranges are completed to select the single measurement with the minimum percentage root mean square as the final reported first complete and fully converged set of parameters and second complete and fully converged set of parameters.

In further embodiments, the plurality of subranges within the excitation frequency range are generated by increasing the minimum frequency in repeated intervals and reducing the maximum frequency in repeated intervals. For example, in some embodiments, the minimum frequency is increased in approximately 5 Hz intervals and the maximum frequency is reduced in approximately 25 Hz intervals. With a excitation frequency range of approximately 40 Hz to approximately 1200 Hz a non-exhaustive listing of approximations of the subranges includes 45 Hz to 1200 Hz, 50 Hz to 1200 Hz, 55 Hz to 1200 Hz, 60 Hz to 1200 Hz, 65 Hz to 1200 Hz, 70 Hz to 1200 Hz, 40 Hz to 1175 Hz, 40 Hz to 1150 Hz, 40 Hz to 1125 Hz, 40 Hz to 1100 Hz, 40 Hz to 1075 Hz, 45 Hz to 1175 Hz, 45 Hz to 1150 Hz, 45 Hz to 1125 Hz, 45 Hz to 1100 Hz, 50 Hz to 1175 Hz, 50 Hz to 1150 Hz, 50 Hz to 1125 Hz, 50 Hz to 1100 Hz, and 50 Hz to 1075 Hz.

In further embodiments, various repeated intervals of increase for the minimum frequency ranging from approximately 1 Hz to approximately 20 Hz are envisioned and various repeated intervals of reduction for the maximum frequency ranging from approximately 5 Hz to approximately 50 Hz are envisioned with all permutations thereof specifically envisioned. For example, in some embodiments, the minimum frequency is increased in approximately 1 Hz intervals and the maximum frequency is reduced in approximately 5 Hz intervals, alternatively, the minimum frequency is increased in approximately 3 Hz intervals and the maximum frequency is reduced in approximately 10 Hz intervals, alternatively, the minimum frequency is increased in approximately 10 Hz intervals and the maximum frequency is reduced in approximately 20 Hz intervals, alternatively, the minimum frequency is increased in approximately 10 Hz intervals and the maximum frequency is reduced in approximately 30 Hz intervals, alternatively, the minimum frequency is increased in approximately 5 Hz intervals and the maximum frequency is reduced in approximately 20 Hz intervals, alternatively, the minimum frequency is increased in approximately 20 Hz intervals and the maximum frequency is reduced in approximately 50 Hz intervals.

In various embodiments, the minimum frequency is increased in repeated intervals until reaching a threshold minimum frequency. Similarly, the maximum frequency is reduced in repeated intervals until reaching a threshold maximum frequency. For example, in an embodiment, the minimum frequency is increased in approximately 5 Hz intervals until reaching a threshold minimum frequency of approximately 180 Hz and the maximum frequency is reduced in approximately 25 Hz intervals until reaching a threshold maximum frequency of approximately 700 Hz. In other embodiments, the threshold minimum frequency is 120, 140, 160, 180, or 200 and the threshold maximum frequency is 650, 700, 750, 800, or 850 with each combination thereof specifically envisioned. The threshold minimum and threshold maximum frequencies ensure that the plurality of subranges generated in the excitation frequency range all include the range between the threshold minimum frequency and the threshold maximum frequency as the minimum frequency is never higher than the threshold minimum frequency nor lower than the threshold maximum frequency. With reference to FIGS. 2 and 3, the threshold minimum and threshold maximum frequencies are selected such that the bone peak 20 of Y(f) and the skin peak 22 of Y(f) are contained within the frequency range enclosed by the threshold minimum frequency and the threshold maximum frequency. Typically, the bone peak 20 of Y(f) is centered at approximately 150-250 Hz and the skin peak of Y(f) is centered at approximately 500-800 Hz. In a further embodiment, the threshold minimum frequency is selected as the resonant frequency representing the bone peak and the threshold maximum frequency is selected as the resonant frequency representing the skin peak.

In various embodiments, each determination of the stiffness of the bone requires approximately 1 minute. Specifically, applying the superposition of static and oscillatory forces (F) over a range of frequencies (f) to a region of the skin-bone complex, receiving the oscillatory forces as functions of time F(t) and oscillatory accelerations as functions of time a(t), and the subsequent fitting of the parametric mathematical model to Y(f) and H(f) takes about 1 minute. The static and oscillatory forces (F) are then applied to the shifted region and a revised stiffness of bone is generated along with a revised measure of conformity; this measurement and analysis also requires approximately 1 minute. Typically, in some embodiments, approximately 15 parameter sets are obtained before the optimized parameter set is determined yielding an elapsed testing time of approximately 15 minutes for the patient. It will be appreciated that determination of each parameter set includes 10s, 100s, or 1000s of individual measurements at frequency sub-ranges.

The optimized parameter set represents the parameter set which is believed to most closely reflect a true and accurate parameter set. The optimized parameter set may be determined by selecting the parameter set having the minimum first measure of conformity, second measure of conformity, or first and second measures of conformity of the entirety of the parameter sets obtained from all the tested skin-bone complex locations. As such, a first complete and fully converged set of parameters and a second complete and fully converged set of parameters are obtained from 100s, 1000s, or 10,000s of measurements at differing locations, rotational positions, and frequency ranges with the optimized parameter set representing the specific measurement which produced the minimized first and second measures of conformity. It will be appreciated that the optimized parameter set may additionally represent an average or other weighting protocol of a set of the parameter sets representing those with the 2, 3, 4, 5, 10, or 25 lowest first and second measures of conformity.

Figure 5:
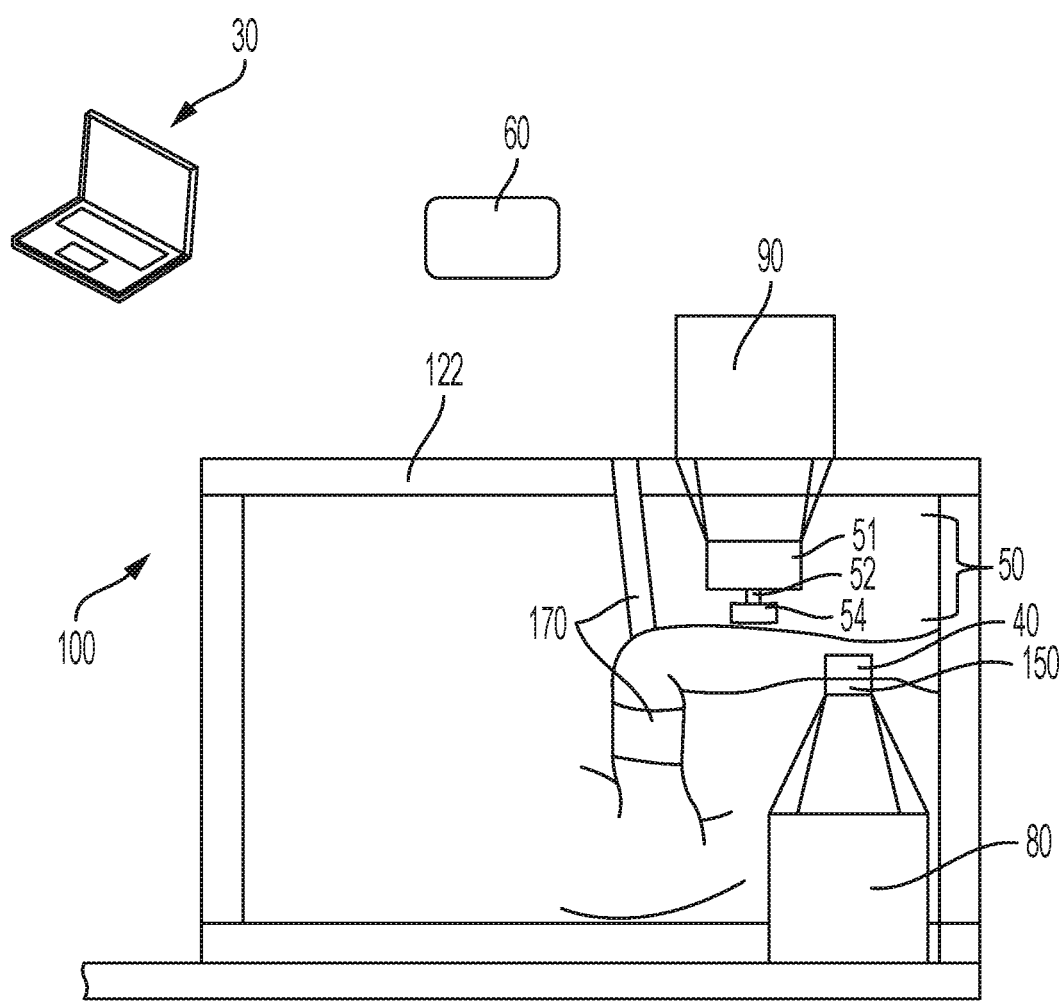
FIG. 5 depicts a side view of a system for estimating the stiffness of a bone in vivo according to at least one embodiment.
Figure 6:
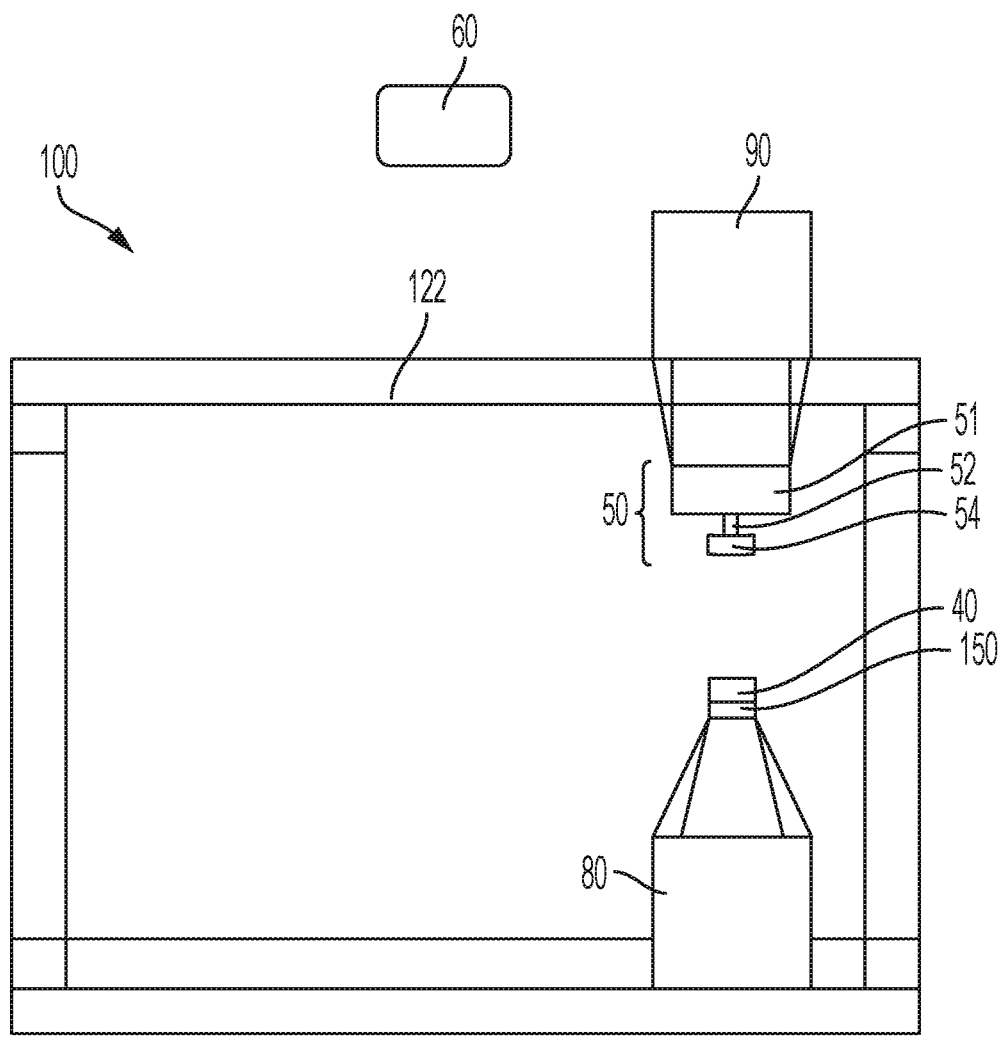
FIG. 6 depicts a front view of a system for estimating the stiffness of a bone in vivo according to at least one embodiment.

Referring to FIGS. 5 and 6, in further embodiments, a system for estimating the stiffness of a bone in vivo is provided. The system includes a device for measuring the stiffness of the bone in vivo as well as a data analyzer 30. In various embodiments the device for measuring the stiffness of the bone in vivo includes a bone positioning support 40, a mechanical force applicator 50, and a frequency response recorder 60. The bone positioning support 40 is configured to position and support the skin-bone complex at the wrist in an orientation and position for measurement. The mechanical force applicator 50 includes a mechanical force generator 51, a sensor 52 measuring static and oscillatory force and acceleration, and a force probe 54 and is configured to apply static and oscillatory forces (F) to a region of the skin-bone complex. The static and oscillatory forces (F) applied to the skin-bone complex by the mechanical force applicator 50 include oscillatory forces (F) which in turn create oscillatory accelerations (a) of the skin-bone complex. Finally, the frequency response recorder 60 is configured to measure and transmit to the data analyzer 30, e.g. a computer, the oscillatory forces (F) and the oscillatory accelerations (a). In embodiments such as those shown in FIGS. 5 and 6, the frequency response recorder 60 is located outside the body of the data analyzer 30. In other embodiments, the frequency response recorder 60 may be located inside the body of the data analyzer 30. The system may further include an open framework 100 of rigid members to support and orient components of the system.

Figure 7A:
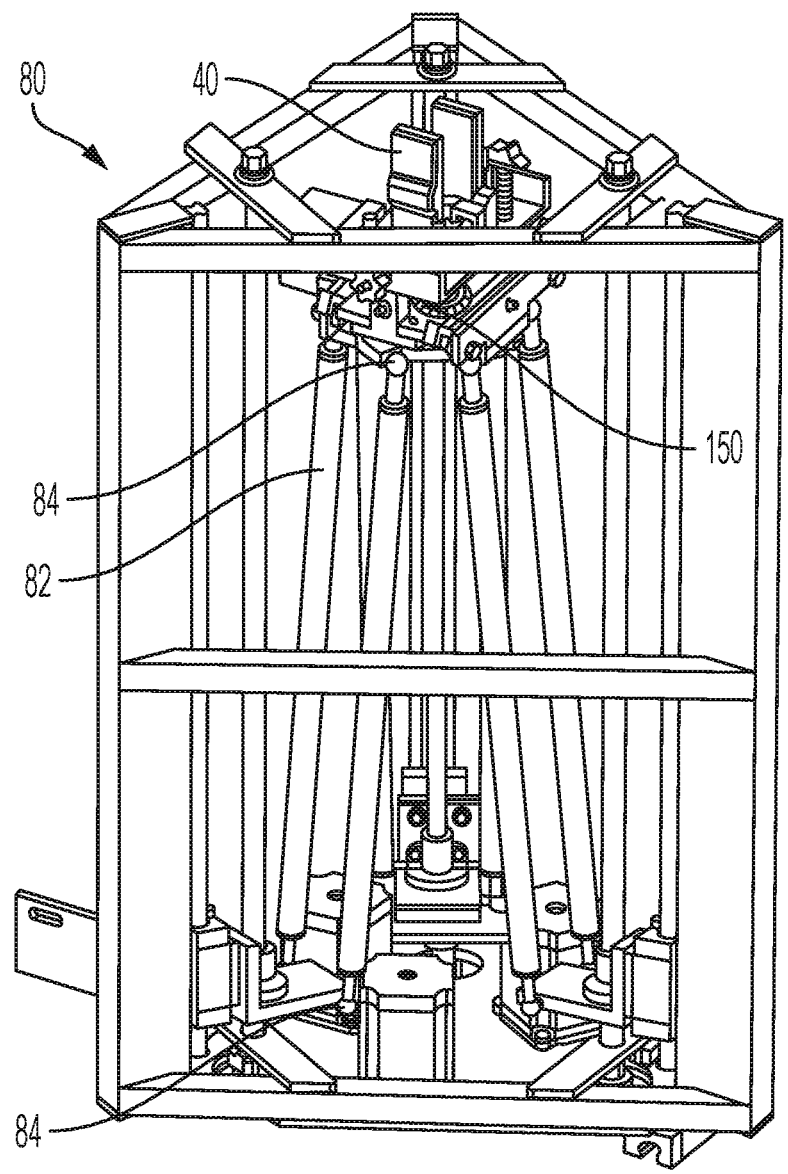
FIG. 7A depicts an inverted delta robot in a retracted position for positioning a patient's wrist according to at least one embodiment.
Figure 7B:
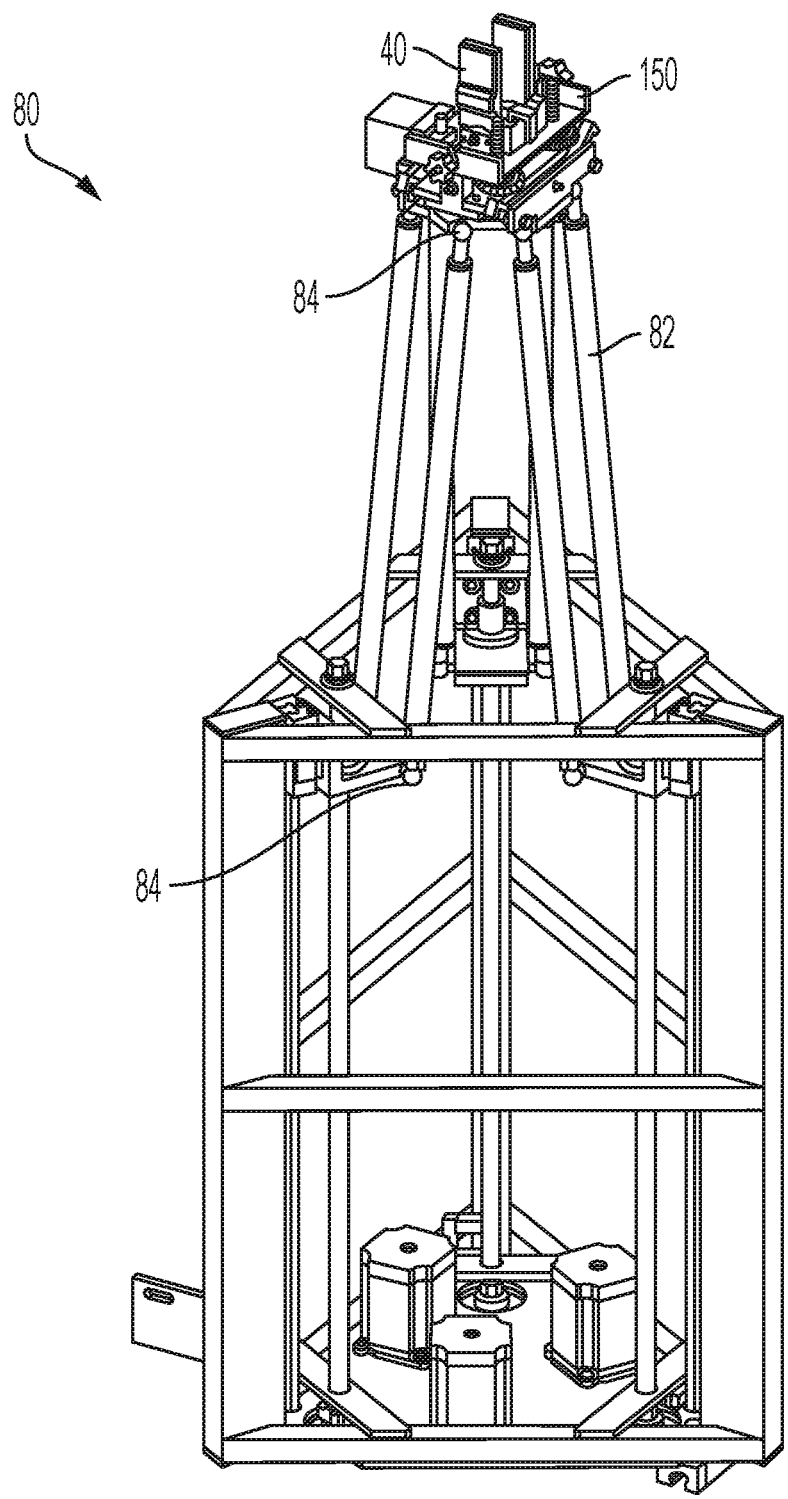
FIG. 7B depicts an inverted delta robot in an extended position for positioning a patient's wrist according to at least one embodiment.

In embodiments, the bone positioning support 40 is connected to an inverted delta robot 80 as illustrated in FIGS. 7A and 7B. As one skilled in the art knows, a delta robot is a type of parallel robot which consists of three pairs of arms 82 connected to joints 84 with at least two degrees of freedom, such as universal joints, at each end. One key design feature of the inverted delta robot 80 is the use of parallelograms in the arms 82, which allows for the orientation of the bone positioning support 40 affixed to the arms 82 of the inverted delta robot 80 to be maintained. The wrist of the patient is supported by the bone positioning support 40 and the inverted delta robot 80 may then controllably position the wrist in X, Y and Z directions. The inverted delta robot 80 may be affixed in a rigid or movable manner to the open framework 100. In further embodiments, the inverted delta robot 80 may be affixed in a rigid or movable manner to the floor or other base structure in the clinical environment.

In some embodiments a bone positioning harness 170 provides support and positioning of the patient's elbow. The bone positioning harness 170 is an adjustable and flexible but inelastic tensile sling attachable to an open framework or other support structure in the system. In some embodiments, the bone positioning harness 170 is attachable to and/or attached to an elevated horizontal member 122 of the open framework 100 such that it is suspended therefrom. In further embodiments, the bone positioning harness 170 is suspended from the open framework on or toward the contralateral side of the patient's body so that the supported humerus is pulled medially against retarding muscular and ligamentous tension in the patient's own shoulder joint. In some embodiments the bone positioning support 40 includes a horizontal platform to support the wrist. In embodiments the horizontal platform is attached to a platform carriage 150 which provides rotational control of the patient's wrist.

In embodiments, the mechanical force applicator 50 the frequency response recorder 60 are connected to a second delta robot 90. The second delta robot 90 may be affixed in a rigid or movable manner to the open framework 100 or other support structure in the system. In further embodiments, the second delta robot 90 may be affixed in a rigid or movable manner to the ceiling or other base structure in the clinical environment. The second delta robot 90 positions the mechanical force applicator 50 on the patient's arm and thereby the static preload force may be adjusted. Furthermore, the second delta robot 90 supports the orientation of the mechanical force applicator 50 so that the linear motion of the mechanical force applicator 50 is along a vertical direction onto the patient's arm. The X, Y, and Z directional positioning of the second delta robot 90 allows the mechanical force applicator 50 to be appropriately positioned on the patient's arm and accommodates patients of differing sizes.

In further embodiments, the portion of the bone positioning support 40 configured to support a distal end of a human forearm comprises at least one layer of viscoelastic material thereon to dampen extraneous oscillatory forces (F) from the device. Dampening extraneous oscillatory forces (F) from the device may function to provide a cleaner and/or more pure data set that better conforms to the 7-parameter model.

In various embodiments, the mechanical force applicator 50 comprises a force generator 51, force and acceleration sensors 52 and a force probe 54. The force generator 51 provides the static and oscillatory forces via the force probe 54. The force generator 51 provides the oscillatory forces (F) when driven by an oscillatory electrical control signal and the static force when driven by a constant electrical control signal to the force probe 54. In further embodiments, the force generator 51 provides the oscillatory forces (F) to the force probe 54 and the static force is provided by manually or electromechanically moving the second delta robot 90 which carries the mechanical force applicator 50, such as previously discussed above.

In further embodiments the mechanical force applicator 50 includes a layer of viscoelastic material placed between the force probe 54 and the skin overlying the bone, thereby supplementing the stiffness of the skin. The layer of viscoelastic material may be affixed to the force probe 54 on the face contacting the skin or may be a separate element loosely provided between the force probe 54 and the skin. Additionally, the viscoelastic material may be provided between the skin and the horizontal platform 150.

In various embodiments of a system for estimating the stiffness of a bone in vivo, the data analyzer 30 is communicatively coupled to the force generator 51 and the force and acceleration sensor 52 and frequency response recorder 60 and the data analyzer 30 includes a storage medium and a processor. The storage medium contains computer readable and executable instructions for collecting the transmitted oscillatory forces as functions of time F(t) and oscillatory accelerations as functions of time a(t) of the skin-bone complex from the frequency response recorder. Additionally, the storage medium stores a parametric model of the skin-bone complex, such as was previously discussed above. The processor is provided for executing the instructions to transform a(t) and F(t) to functions of frequency, a(f) and F(f). The processor is also provided for executing the instructions to reduce a(f) and F(f) to accelerance frequency response data A(f) such as previously discussed. Further, the processor is provided for executing the instructions to determine a complex compliance frequency response function Y(f) and associated complex stiffness frequency response function H(f), to fit the parametric mathematical model to Y(f) to obtain a first complete and fully converged set of parameters of the parametric mathematical model, including the stiffness of the bone ($K_B$), and to fit the parametric mathematical model to H(f) to obtain a second complete and fully converged set of parameters of the parametric mathematical model, including the stiffness of the bone ($K_B$), such as previously discussed. Further, the processor determines the discrepancies between the first complete and fully converged set of parameters and the second complete and fully converged set of parameters as a first measure of conformity thereof to the parametric mathematical model, such as previously discussed above. The process also determines a second measure of conformity between the skewness and kurtosis of the bone peak in the imaginary part of the complex compliance frequency response function and the parametric mathematical model.

In further embodiments of a system for estimating the stiffness of a bone in vivo, the processor is connected to a visual subsystem with a graphical user interface (GUI). The visual subsystem and graphical user interface provides information to the technician and/or operator of the system. In various embodiments, the information provided to the technician and/or operator includes displays of the fit of the parametric mathematical model to the accelerance frequency response function data A(f), the complex compliance frequency response function Y(f), and/or the complex stiffness frequency response function H(F). For example, graphical display of a curve representing experimental Y(f), H(f), and/or A(f) may be displayed with a curve generated by the best fit parameters overlaid in each instance. Additionally, statistical indicators of the fit of the parametric mathematical model to the accelerance frequency response function data A(f), the complex compliance frequency response function Y(f), and/or the complex stiffness frequency response function H(F) may be provided, such as in tabular form. For example, $R^2$ and RMS and SnK may be provided to indicate the goodness of the best fit parameters to the complex compliance frequency response function Y(f) and/or the complex stiffness frequency response function H(F).

Additionally, a method for determining the stiffness of a bone is provided. The method may be practiced using the system previously discussed. The method comprises applying a controlled superposition of static force and oscillatory force (F) measured as a first function of frequency F(f) spanning a range of frequencies to a skin-bone complex in vivo. The applied controlled oscillatory forces (F) thereby excite oscillatory accelerations (a) over the range of frequencies of the skin-bone complex. Then the resulting oscillatory accelerations (a) of the skin-bone complex are measured as a second function of frequency a(f). Further, as discussed in the previous method, F(f) and a(f) are transformed to obtain the stiffness of the skin-bone complex as a function of frequency H(f). Additionally, as previously discussed above, F(f) and a(f) are transformed to obtain the compliance of the skin-bone complex as a function of frequency Y(f). Then a parametric model is fit to H(f) to obtain a first set of parameters of the parametric model, including the stiffness of the bone $K_B$. Further, the parametric model is fit to Y(f) to obtain a second set of parameters of the parametric model, including the stiffness of the bone. As previously discussed above, discrepancies between the first set of parameters and the second set of parameters as a first measure of conformity thereof to the parametric mathematical model are determined. Additionally, a second measure of conformity between the skewness and kurtosis of the bone beak in the complex compliance frequency response function and the parametric mathematical model are determined. The first measure of conformity, the first set of parameters, the second set of parameters, and the second measure of conformity are saved as a parameter set.

Further, in an effort to obtain an optimized parameter set, the static and oscillatory forces (F) are applied to a shifted region of the skin-bone complex and the oscillatory forces (F) and the resulting oscillatory accelerations (a) for the shifted region are measured. Further, as discussed in the previous method, F(f) and a(f) of the shifted region measurements are transformed to obtain the stiffness of the skin-bone complex as a function of frequency H(f). Additionally, as previously discussed above, F(f) and a(f) of the shifted region measurements are also transformed to obtain the compliance of the skin-bone complex as a function of frequency Y(f). Then the parametric model is fit to H(f) to obtain a new first set of parameters of the parametric model, including the stiffness of the bone, and the parametric model is also fit to Y(f) to obtain a new second set of parameters of the parametric model, including the stiffness of the bone. Repetition of collection of the oscillatory forces (F) and the resulting oscillatory accelerations (a) for shifted regions and analysis of the collected oscillatory forces (F) and oscillatory accelerations (a) to determine parameters of the parametric mathematical model is continued until the optimized parameter set is determined. Finally, the stiffness of the bone is determined from ($K_B$) values of the optimized parameter set as previously discussed above.

It should now be understood that various aspects of the disclosed method and system are described herein and that such aspects may be utilized in conjunction with various other aspects.

Having shown and described various embodiments in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

As will be evident from the foregoing disclosure, the methods of the invention are carried out non-invasively. Additionally, the methods of the invention can be carried out by technicians without medical training and in the absence of medical supervision.

The invention claimed is:

1. A system for estimating the stiffness of a bone in vivo, the system comprising a device for measuring the stiffness of the bone in vivo and a data analyzer:
   the device for measuring the stiffness of the bone in vivo comprising a bone support, a mechanical force applicator, and a frequency response recorder, wherein:
   the bone support is configured to position and support a skin-bone complex in an orientation and position for measurement;
   the mechanical force applicator comprises static and oscillatory force generator, static and oscillatory force sensors, an acceleration sensor, and a force probe and is configured to apply a superposition of controlled static and oscillatory forces (F) over a range of frequencies (f) to a region of the skin-bone complex, wherein the oscillatory forces (F) excite oscillatory accelerations (a) of the skin-bone complex; and
   the frequency response recorder is configured to measure and transmit to the data analyzer the oscillatory forces as functions of time F(t) and the oscillatory accelerations as functions of time a(t); and
   the data analyzer communicatively coupled to the static and oscillatory force generator, the static and oscillatory force sensors, the acceleration sensor, and frequency response recorder and comprising:
   a storage medium containing computer readable and executable instructions for collecting the transmitted oscillatory forces as functions of time F(t) and oscillatory accelerations as functions of time a(t) of the skin-bone complex, the storage medium storing a parametric mathematical model of the skin-bone complex; and
   a processor for executing the instructions to transform a(t) and F(t) to functions of frequency, a(f) and F(f), to reduce a(f) and F(f) to accelerance frequency response data A(f), to determine a complex compliance frequency response function Y(f) and associated complex stiffness frequency response function H(f), to fit the parametric mathematical model to Y(f) to obtain a first complete and fully converged set of parameters of the parametric mathematical model, including the stiffness of the bone ($K_B$), to independently fit the parametric mathematical model to H(f) to obtain a second complete and fully converged set of parameters of the parametric mathematical model, including the stiffness of the bone ($K_B$), to determine the discrepancies between the first complete and fully converged set of parameters and the second complete and fully converged set of parameters as a first measure of conformity thereof to the parametric mathematical model, and to determine a second measure of conformity between the skewness of the bone peak in the complex compliance frequency response function and the parametric mathematical model and between the kurtosis of the bone peak in the complex compliance frequency response function and the parametric mathematical model.

2. The system of claim 1, wherein the first measure of conformity between the first complete and fully converged set of parameters and the second complete and fully converged set of parameters is quantified as a root mean square therebetween of the percentage differences between each of the parameters of the first complete and fully converged set of parameters and the second complete and fully converged set of parameters.

3. The system of claim 1, wherein the second measure of conformity is the sum of the absolute differences between:
   (a) the skewness of the bone peak in the complex frequency response function and the characteristic value of the skewness of the bone peak in the parametric mathematical model, and
   (b) the kurtosis of the bone peak in the complex frequency response function and the characteristic value of the kurtosis of the bone peak in the parametric mathematical model.

4. The system of claim 1, wherein the parametric model of the skin-bone complex includes seven parameters comprising mass of the skin ($M_S$), transverse bending stiffness of the skin ($K_S$), damping coefficient of the skin ($B_S$) mass of the bone ($M_B$), transverse bending stiffness of the bone ($K_B$), damping coefficient of the bone ($B_B$), and damping coefficient of surrounding soft tissue ($B_P$).

5. The system of claim 4, wherein the oscillatory forces (F) are applied to the skin-bone complex through an excitation frequency range having a minimum frequency of approximately 40 Hz and a maximum frequency of approximately 1200 Hz.

6. The system of claim 5, wherein
   the parametric mathematical model is repeatedly fit to Y(f) and H(f) at a plurality of subranges within the excitation frequency range;
   a root mean square of the percentage differences between each of the parameters of the first complete and fully converged set of parameters and the second complete and fully converged set of parameters is quantified with the algorithm processor, for each of the plurality of subranges within the excitation frequency range;

a minimum resultant of the root mean square for the plurality of subranges is used as the measure of conformity; and the second measure of conformity in step (vii) is the sum of the absolute differences between:
(a) the skewness of the bone peak in the complex frequency response function and the characteristic value of the skewness of the bone peak in the parametric mathematical model, and
(b) the kurtosis of the bone peak in the complex frequency response function and the characteristic value of the kurtosis of the bone peak in the parametric mathematical model.

7. The system of claim 6, wherein the plurality of subranges within the excitation frequency range are generated by increasing the minimum frequency in approximately 1 to 10 Hz intervals and reducing the maximum frequency in approximately 1 to 40 Hz intervals.

8. The system of claim 7, wherein the minimum frequency is increased in approximately 5 Hz intervals until reaching approximately 180 Hz and the maximum frequency is decreased in approximately 25 Hz intervals until reaching approximately 700 Hz.

9. The system of claim 7, wherein the minimum frequency is increased until reaching a resonant frequency representing a bone peak and the maximum frequency is decreased until reaching a resonant frequency representing a skin peak.

\* \* \* \* \*